US009706647B2

(12) United States Patent
Hsu et al.

(10) Patent No.: US 9,706,647 B2
(45) Date of Patent: Jul. 11, 2017

(54) CONFORMAL ELECTRONICS INCLUDING NESTED SERPENTINE INTERCONNECTS

(71) Applicant: MC10, INC., Cambridge, MA (US)

(72) Inventors: Yung-Yu Hsu, Arlington, MA (US); John Work, Somerville, MA (US); Kevin J. Dowling, Westford, MA (US)

(73) Assignee: MC10, INC., Lexington, MA (US)

( * ) Notice: Subject to any disclaimer, the term of this patent is extended or adjusted under 35 U.S.C. 154(b) by 352 days.

(21) Appl. No.: 14/276,413

(22) Filed: May 13, 2014

(65) Prior Publication Data

US 2014/0340857 A1 Nov. 20, 2014

Related U.S. Application Data

(60) Provisional application No. 61/823,357, filed on May 14, 2013.

(51) Int. Cl.
| | |
|---|---|
| *H05K 1/02* | (2006.01) |
| *A61B 5/00* | (2006.01) |
| *H01L 23/538* | (2006.01) |
| *H05K 1/18* | (2006.01) |
| *H01L 23/14* | (2006.01) |

(52) U.S. Cl.
CPC ......... *H05K 1/0283* (2013.01); *A61B 5/6846* (2013.01); *H01L 23/5386* (2013.01); *H01L 23/5387* (2013.01); *A61B 5/0059* (2013.01); *A61B 2562/164* (2013.01); *H01L 23/145* (2013.01); *H01L 2924/15791* (2013.01); *H05K 1/189* (2013.01); *H05K 2201/0133* (2013.01); *H05K 2201/0394* (2013.01); *H05K 2201/09263* (2013.01); *H05K 2201/09945* (2013.01)

(58) Field of Classification Search
None
See application file for complete search history.

(56) References Cited

U.S. PATENT DOCUMENTS

| | | |
|---|---|---|
| 7,265,298 B2 | 9/2007 | Maghribi |
| 7,337,012 B2 | 2/2008 | Maghribi |
| 7,487,587 B2 | 2/2009 | Vanfleteren |
| 7,491,892 B2 | 2/2009 | Wagner |

(Continued)

FOREIGN PATENT DOCUMENTS

| | | |
|---|---|---|
| WO | WO 2005/122285 A2 | 12/2005 |
| WO | WO 2008/030960 A2 | 3/2008 |

(Continued)

OTHER PUBLICATIONS

International Search Report, application No. PCT/US2014/038002, dated Dec. 23, 2014, 5 pages.

(Continued)

*Primary Examiner* — Courtney Smith
*Assistant Examiner* — Jessey R Ervin
(74) *Attorney, Agent, or Firm* — Nixon Peabody LLP

(57) ABSTRACT

An example stretchable device is described that includes electrical contacts and an interconnect coupling the electrical contacts. The interconnect has a meander-shaped configuration that includes at least one nested serpentine-shaped feature. The interconnect can be conductive or non-conductive. The meander-shaped configuration can be a serpentine structure, providing a serpentine-in-serpentine configuration.

18 Claims, 18 Drawing Sheets

(56) References Cited

U.S. PATENT DOCUMENTS

| | | | |
|---|---|---|---|
| 7,521,292 B2 | 4/2009 | Rogers | |
| 7,557,367 B2 | 7/2009 | Rodgers | |
| 7,622,367 B1 | 11/2009 | Nuzzo | |
| 7,759,167 B2 | 7/2010 | Vanfleteren | |
| 7,960,246 B2 | 6/2011 | Flamand | |
| 7,982,296 B2 | 7/2011 | Nuzzo | |
| 8,055,353 B2* | 11/2011 | Kreidler | A61N 1/05 607/122 |
| 8,097,926 B2 | 1/2012 | De Graff | |
| 8,198,621 B2 | 6/2012 | Rogers | |
| 8,207,473 B2* | 6/2012 | Axisa | B32B 37/185 174/254 |
| 8,217,381 B2 | 7/2012 | Rodgers | |
| 8,372,726 B2 | 2/2013 | De Graff | |
| 8,389,862 B2 | 3/2013 | Arora | |
| 8,431,828 B2 | 4/2013 | Vanfleteren | |
| 8,440,546 B2 | 5/2013 | Nuzzo | |
| 8,536,667 B2 | 9/2013 | De Graff | |
| 8,552,299 B2 | 10/2013 | Rodgers | |
| 8,664,699 B2 | 3/2014 | Nuzzo | |
| 8,679,888 B2 | 3/2014 | Rodgers | |
| 8,729,524 B2 | 5/2014 | Rodgers | |
| 8,754,396 B2 | 6/2014 | Rogers | |
| 8,865,489 B2 | 10/2014 | Rodgers | |
| 8,886,334 B2 | 11/2014 | Ghaffari | |
| 8,905,772 B2 | 12/2014 | Rodgers | |
| 2002/0094701 A1 | 7/2002 | Biegelsen | |
| 2003/0214408 A1 | 11/2003 | Grajales | |
| 2004/0094762 A1 | 5/2004 | Hess | |
| 2004/0232910 A1 | 11/2004 | Ciplickas | |
| 2004/0238819 A1 | 12/2004 | Maghribi | |
| 2004/0243204 A1 | 12/2004 | Maghribi | |
| 2006/0038182 A1 | 2/2006 | Rodgers | |
| 2006/0286785 A1 | 12/2006 | Rogers | |
| 2007/0248799 A1 | 10/2007 | Deangelis | |
| 2008/0046080 A1 | 2/2008 | Vanden Bulcke | |
| 2008/0157235 A1 | 7/2008 | Rodgers | |
| 2008/0204021 A1 | 8/2008 | Leussler et al. | |
| 2009/0107704 A1 | 4/2009 | Vanfleteren | |
| 2009/0261828 A1 | 10/2009 | Nordmeyer-Massner | |
| 2009/0294803 A1 | 12/2009 | Nuzzo | |
| 2010/0002402 A1 | 1/2010 | Rodgers | |
| 2010/0059863 A1 | 3/2010 | Rogers | |
| 2010/0072577 A1 | 3/2010 | Nuzzo | |
| 2010/0087782 A1 | 4/2010 | Ghaffari | |
| 2010/0116526 A1 | 5/2010 | Arora | |
| 2010/0178722 A1 | 7/2010 | De Graff | |
| 2010/0271191 A1 | 10/2010 | De Graff | |
| 2010/0298895 A1 | 11/2010 | Ghaffari | |
| 2010/0317132 A1 | 12/2010 | Rodgers | |
| 2010/0321161 A1 | 12/2010 | Isabell | |
| 2011/0034912 A1 | 2/2011 | De Graff | |
| 2011/0054583 A1 | 3/2011 | Litt | |
| 2011/0184320 A1 | 7/2011 | Shipps | |
| 2011/0215931 A1 | 9/2011 | Callsen | |
| 2011/0218756 A1 | 9/2011 | Callsen | |
| 2011/0218757 A1 | 9/2011 | Callsen | |
| 2011/0220890 A1 | 9/2011 | Nuzzo | |
| 2011/0277813 A1 | 11/2011 | Rodgers | |
| 2012/0051005 A1 | 3/2012 | Vanfleteren | |
| 2012/0052268 A1 | 3/2012 | Axisa | |
| 2012/0065937 A1 | 3/2012 | De Graff | |
| 2012/0092178 A1 | 4/2012 | Callsen | |
| 2012/0157804 A1* | 6/2012 | Rogers | A61B 5/0422 600/345 |
| 2012/0172697 A1 | 7/2012 | Urman | |
| 2012/0226130 A1 | 9/2012 | De Graff | |
| 2012/0244848 A1 | 9/2012 | Ghaffari | |
| 2012/0256308 A1 | 10/2012 | Helin | |
| 2012/0327608 A1 | 12/2012 | Rodgers | |
| 2013/0041235 A1 | 2/2013 | Rodgers | |
| 2013/0099358 A1 | 4/2013 | Elolampi | |
| 2013/0100618 A1 | 4/2013 | Rogers | |
| 2013/0118255 A1 | 5/2013 | Callsen | |
| 2013/0150693 A1 | 6/2013 | D'Angelo | |
| 2013/0185003 A1 | 7/2013 | Carbeck | |
| 2013/0192356 A1 | 8/2013 | De Graff | |
| 2013/0200268 A1 | 8/2013 | Rafferty | |
| 2013/0225965 A1 | 8/2013 | Ghaffari | |
| 2013/0245388 A1 | 9/2013 | Rafferty | |
| 2013/0274562 A1 | 10/2013 | Ghaffari | |
| 2013/0313713 A1 | 11/2013 | Arora | |
| 2013/0316487 A1 | 11/2013 | De Graff | |
| 2013/0320503 A1 | 12/2013 | Nuzzo | |
| 2014/0001058 A1 | 1/2014 | Ghaffari | |
| 2014/0012160 A1 | 1/2014 | Ghaffari | |
| 2014/0012242 A1 | 1/2014 | Lee | |
| 2014/0022746 A1 | 1/2014 | Hsu | |
| 2014/0039290 A1 | 2/2014 | De Graff | |
| 2014/0097944 A1 | 4/2014 | Fastert | |
| 2014/0110859 A1 | 4/2014 | Rafferty | |
| 2014/0140020 A1 | 5/2014 | Rodgers | |
| 2014/0188426 A1 | 7/2014 | Fastert | |
| 2014/0191236 A1 | 7/2014 | Nuzzo | |
| 2014/0216524 A1 | 8/2014 | Rodgers | |
| 2014/0240932 A1 | 8/2014 | Hsu | |
| 2014/0249520 A1 | 9/2014 | Ghaffari | |
| 2014/0303452 A1 | 10/2014 | Ghaffari | |
| 2014/0340857 A1 | 11/2014 | Hsu | |
| 2014/0374872 A1 | 12/2014 | Rodgers | |
| 2014/0375465 A1 | 12/2014 | Fenuccio | |
| 2015/0001462 A1 | 1/2015 | Rogers | |
| 2015/0019135 A1 | 1/2015 | Kacyvenski | |
| 2015/0035680 A1 | 2/2015 | Li | |

FOREIGN PATENT DOCUMENTS

| | | | |
|---|---|---|---|
| WO | WO 2009/111641 A1 | 9/2009 | |
| WO | WO 2009/114689 A1 | 9/2009 | |
| WO | WO 2010/036807 A1 | 4/2010 | |
| WO | WO 2010/042653 A1 | 4/2010 | |
| WO | WO 2010/042957 A2 | 4/2010 | |
| WO | WO 2010/056857 A2 | 5/2010 | |
| WO | WO 2010/081137 A2 | 7/2010 | |
| WO | WO 2010/082993 A2 | 7/2010 | |
| WO | WO 2010/102310 A2 | 9/2010 | |
| WO | WO 2010/132552 A1 | 11/2010 | |
| WO | WO 2011/003181 A1 | 1/2011 | |
| WO | WO 2011/041727 A1 | 4/2011 | |
| WO | WO 2011/084450 A1 | 7/2011 | |
| WO | WO 2011/084709 A2 | 7/2011 | |
| WO | WO 2011/127331 A2 | 10/2011 | |
| WO | WO 2012/125494 A2 | 9/2012 | |
| WO | WO 2012/166686 A2 | 12/2012 | |
| WO | WO 2013/010171 A1 | 1/2013 | |
| WO | WO 2013/022853 A1 | 2/2013 | |
| WO | WO 2013/033724 A1 | 3/2013 | |
| WO | WO 2013/049716 A1 | 4/2013 | |
| WO | WO 2013/052919 A2 | 4/2013 | |
| WO | WO 2014/007871 A1 | 1/2014 | |
| WO | WO 2014/058473 A1 | 4/2014 | |
| WO | WO 2014/059032 A1 | 4/2014 | |
| WO | WO 2014/106041 A1 | 7/2014 | |
| WO | WO 2014/110176 A1 | 7/2014 | |
| WO | WO 2014/130928 A2 | 8/2014 | |
| WO | WO 2014/130931 A1 | 8/2014 | |
| WO | WO 2014/186467 A2 | 11/2014 | |
| WO | WO 2014/197443 A1 | 12/2014 | |
| WO | WO 2014/205434 A2 | 12/2014 | |
| WO | WO 2015/021039 A1 | 2/2015 | |

OTHER PUBLICATIONS

Written Opinion, application No. PCT/US2014/038002, dated Dec. 23, 2014, 6 pages.

Demura et al., "Immobilization of Glucose Oxidase with *Bombyx mori* Silk Fibroin by Only Stretching Treatment and its Application to Glucose Sensor," Biotechnology and Bioengineering, vol. 33, 598-603 (6 pages) (1989).

Halsted, "Ligature and Suture Material," Journal of the American Medical Association, vol. LX, No. 15, 1119-1126, (8 pages) (Apr. 12, 1913).

(56) References Cited

OTHER PUBLICATIONS

Kim et al., "Complementary Metal Oxide Silicon Integrated Circuits Incorporating Monolithically Integrated Stretchable Wavy Interconnects," Applied Physics Letters, vol. 93, 044102-044102.3 (3 pages) (Jul. 31, 2008).
Kim et al., "Dissolvable Films of Silk Fibroin for Ultrathin Conformal Bio-Integrated Electronics," Nature, 1-8 (8 pages) (Apr. 18, 2010).
Kim et al., "Materials and Noncoplanar Mesh Designs for Integrated Circuits with Linear Elastic Responses to Extreme Mechanical Deformations," PNAS, vol. 105, No. 48, 18675-18680 (6 pages) (Dec. 2, 2008).
Kim et al., "Stretchable and Foldable Silicon Integrated Circuits," Science, vol. 320, 507-511 (5 pages) (Apr. 25, 2008).
Ko et al., "A Hemispherical Electronic Eye Camera Based on Compressible Silicon Optoelectronics," Nature, vol. 454, 748-753 (6 pages) (Aug. 7, 2008).
Lawrence et al., "Bioactive Silk Protein Biomaterial Systems for Optical Devices," Biomacromolecules, vol. 9, 1214-1220 (7 pages) (Nov. 4, 2008).
Meitl et al., "Transfer Printing by Kinetic Control of Adhesion to an Elastomeric Stamp," Nature, vol. 5, 33-38 (6 pages) (Jan. 2006).
Omenetto et al., "A New Route for Silk," Nature Photonics, vol. 2, 641-643 (3 pages) (Nov. 2008).
Omenetto et al., "New Opportunities for an Ancient Material," Science, vol. 329, 528-531 (5 pages) (Jul. 30, 2010).
Tsukada et al., "Structural Changes of Silk Fibroin Membranes Induced by Immersion in Methanol Aqueous Solutions," Journal of Polymer Science, vol. 32, 961-968 (8 pages) (1994).
Wang et al., "Controlled Release From Multilayer Silk Biomaterial Coatings to Modulate Vascular Cell Responses" Biomaterials, 29, 894-903 (10 pages) (Nov. 28, 2008).
U.S. Appl. No. 12/921,808, filed Mar. 12, 2009, B. Litt, Flexible and Scalable Sensor Arrays for Recording and Modulating Physiologic Activity.
U.S. Appl. No. 12/968,637, filed Dec. 15, 2010, J. Rodgers, High-Speed, High-Resolution Electrophysiology In-Vivo Using Conformal Electronics.
U.S. Appl. No. 13/492,636, filed Jun. 8, 2012, J. Rodgers, Flexible and Stretchable Electronic Systems for Epidermal Electronics.
U.S. Appl. No. 14/155,010, filed Jan. 14, 2014, R. Nuzzo, Methods and Devices for Fabricating and Assembling Printable Semiconductor Elements.
U.S. Appl. No. 14/173,525, filed Feb. 5, 2014, J. Rodgers, Arrays of Ultrathin Silicon Solar Microcells.
U.S. Appl. No. 14/220,910, filed Mar. 20, 2014, J. Rodgers, Controlled Buckling Structures in Semiconductor Interconnnects and Nanomembranes for Stretchable Electronics.
U.S. Appl. No. 14/220,923, filed Mar. 20, 2014, J. Rogers, Stretchable Form of Single Crystal Silicon for High Performance Electronics on Rubber Substrates.
U.S. Appl. No. 14/479,100, filed Sep. 5, 2014, J. Rodgers, Printed Assemblies of Ultrathin, Microscale Inorganic Light Emitting Diodes for Deformable and Semitransparent Displays.
U.S. Appl. No. 14/521,319, filed Oct. 22, 2014, J. Rodgers, Stretchable and Foldable Electronic Devices.

\* cited by examiner

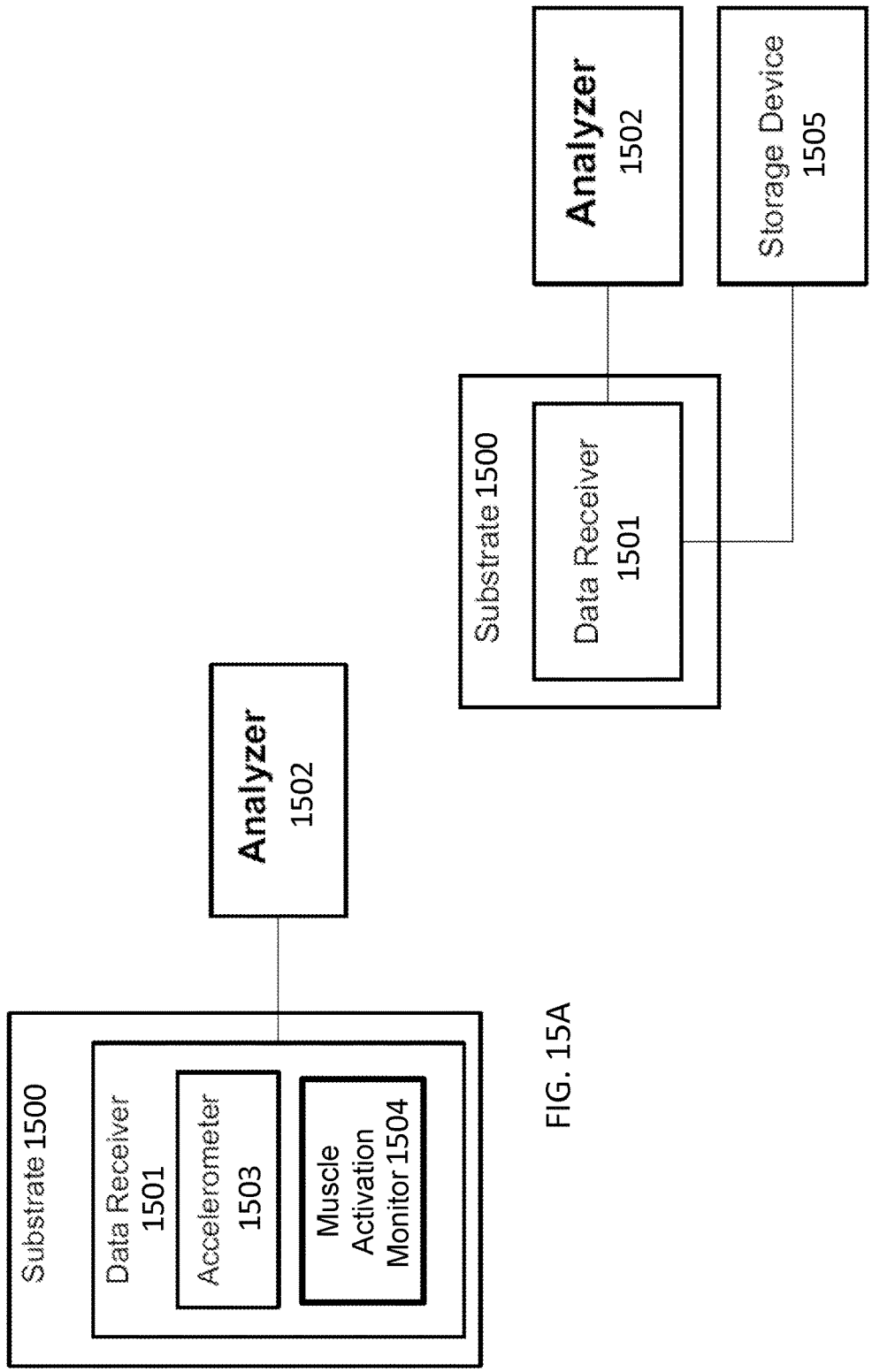

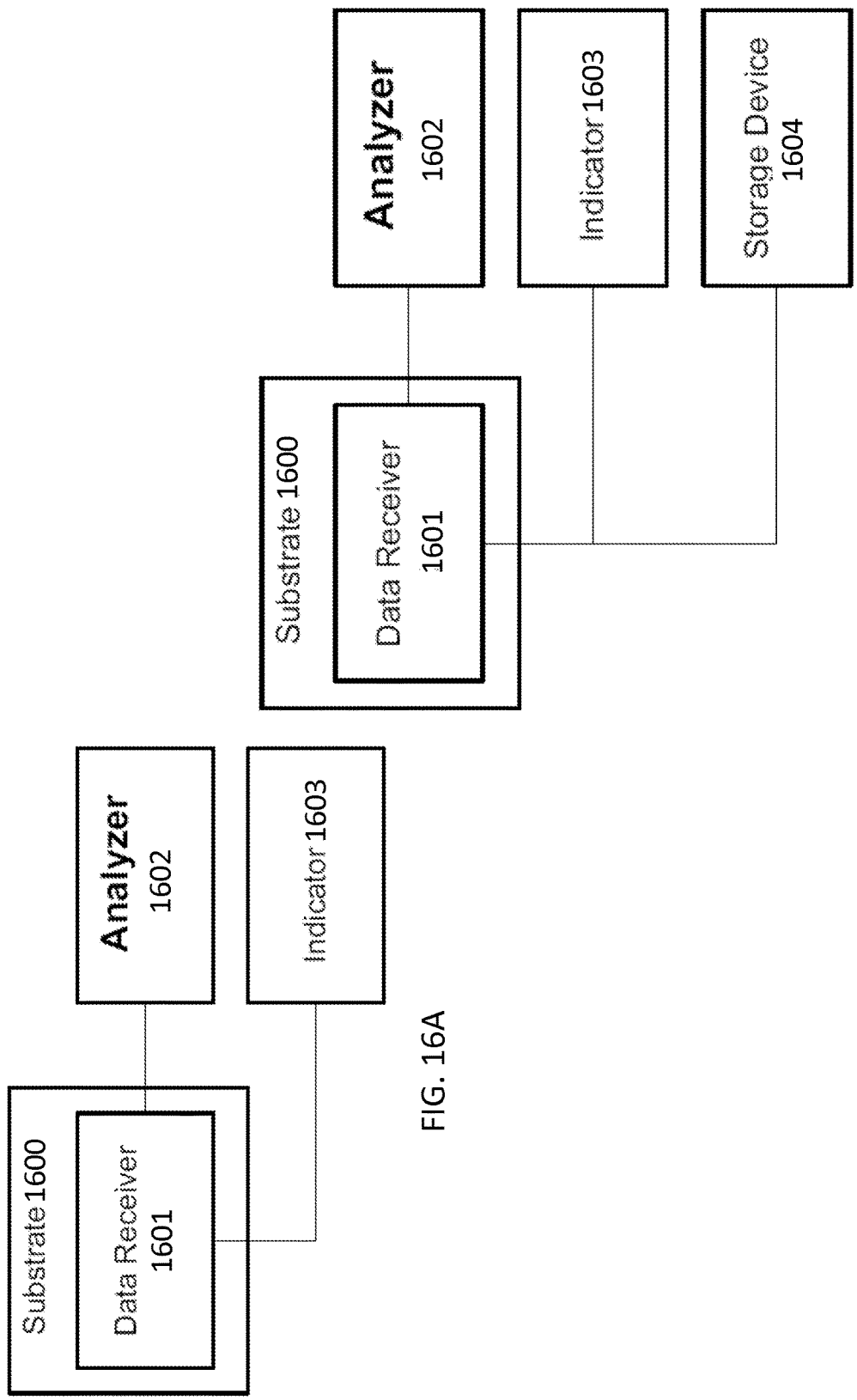

CONFORMAL ELECTRONICS INCLUDING NESTED SERPENTINE INTERCONNECTS

CROSS-REFERENCE TO RELATED APPLICATIONS

This application claims priority to and benefit of U.S. Provisional Application No. 61/823,357, filed on May 14, 2013, entitled "CONFORMAL ELECTRONICS INCLUDING FRACTAL SERPENTINE INTERCONNECTS," which application is incorporated herein by reference in its entirety, including drawings.

BACKGROUND

High quality medical sensing and imaging data has become increasingly beneficial in the diagnoses and treatment of a variety of medical conditions. The conditions can be associated with the digestive system, the cardio-circulatory system, and can include injuries to the nervous system, cancer, and the like. To date, most electronic systems that could be used to gather such sensing or imaging data have been rigid and inflexible. These rigid electronics are not ideal for many applications, such as in biomedical devices. Most of biological tissue is soft and curved. The skin and organs are delicate and far from two-dimensional. Other potential applications of electronics systems, such as for gathering data in non-medical systems, also can be hampered by rigid electronics.

SUMMARY

Various examples described herein are directed generally to methods, apparatus, and systems that include interconnects that provide for greater stretchability and flexibility.

Example methods, apparatus, and systems provide stretchable electrical devices that include two electrical contacts and an electrical interconnect electrically coupling the two electrical contacts.

According to an aspect, the example electrical interconnect can have a meander-shaped configuration that includes at least one nested serpentine-shaped feature.

In an example implementation according to the first aspect, the meander-shaped configuration can be a serpentine structure, a zig-zag structure, a boustrophedonic structure, a rippled structure, a corrugated structure, or a helical structure.

According to an aspect, the example electrical interconnect can have a serpentine-in-serpentine configuration that includes a serpentine-shaped structure including at least one nested serpentine-shaped feature.

The example two electrical contacts can be disposed on an elastomeric substrate.

In an example implementation, the stretchable electrical device can be configured such that two electrical contacts is in physical communication with the elastomeric substrate, and the electrical interconnect is not in physical communication with the substrate.

In an example, at least one of the two electrical contacts can be in communication with a semiconductor circuit.

The example electrical contacts can be metal contacts.

In an example, the stretchable electrical device can include at least one device component in communication with at least one of the two electrical contacts. The at least one device component can be an electronic device component, an optical device component, an optoelectronic device component, a mechanical device component, a microelectromechanical device component, a nanoelectromechanical device component, a microfluidic device component or a thermal device.

Example methods, apparatus, and systems provide stretchable devices that include a stretchable substrate and a stretchable electronic circuit disposed on a surface of the stretchable substrate. The stretchable electronic circuit includes first and second discrete operative devices and a stretchable interconnect coupling the first discrete operative device to the second discrete operative device. The stretchable interconnect can have a meander-shaped configuration that includes at least one nested serpentine-shaped feature.

According to different aspects, the meander-shaped configuration can be a serpentine structure, a zig-zag structure, a boustrophedonic structure, a rippled structure, a corrugated structure, or a helical structure.

According to an aspect, the example stretchable interconnect can have a serpentine-in-serpentine configuration.

In an example, the first discrete operative device or the second discrete operative device can include a metal contact.

In an example, the first discrete operative device or the second discrete operative device is a semiconductor device.

The first and second discrete operative devices and the stretchable interconnect can be fabricated from the same material.

In an example, the same material can be a semiconductor material.

In an example, the stretchable interconnect can be made from a semiconductor material.

The first discrete operative device also can be formed from a semiconductor material. In an example, the stretchable interconnect is made from a different semiconductor material than the first discrete operative device.

In an example, the semiconductor material is a single crystal semiconductor material.

In an example implementation, the stretchable electrical device can be configured such that the first discrete operative device and the second discrete operative device are in physical communication with the surface of the stretchable substrate, and the stretchable interconnect is not in physical communication with the surface.

The first discrete operative device or the second discrete operative device can includes one or more of a photodetector, a photodiode array, a display, a light-emitting device, a photovoltaic device, a sensor array, a light-emitting diode, a semiconductor laser, an optical imaging system, a transistor, a microprocessor, an integrated circuit, or any combination of thereof.

The following publications, patents, and patent applications are hereby incorporated herein by reference in their entirety:

Kim et al., "Stretchable and Foldable Silicon Integrated Circuits," Science Express, Mar. 27, 2008, 10.1126/science.1154367;

Ko et al., "A Hemispherical Electronic Eye Camera Based on Compressible Silicon Optoelectronics," Nature, Aug. 7, 2008, vol. 454, pp. 748-753;

Kim et al., "Complementary Metal Oxide Silicon Integrated Circuits Incorporating Monolithically Integrated Stretchable Wavy Interconnects," Applied Physics Letters, Jul. 31, 2008, vol. 93, 044102;

Kim et al., "Materials and Noncoplanar Mesh Designs for Integrated Circuits with Linear Elastic Responses to Extreme Mechanical Deformations," PNAS, Dec. 2, 2008, vol. 105, no. 48, pp. 18675-18680;

Meitl et al., "Transfer Printing by Kinetic Control of Adhesion to an Elastomeric Stamp," Nature Materials, January, 2006, vol. 5, pp. 33-38;

U.S. Patent Application publication no. 2010 0002402-A1, published Jan. 7, 2010, filed Mar. 5, 2009, and entitled "STRETCHABLE AND FOLDABLE ELECTRONIC DEVICES;"

U.S. Patent Application publication no. 2010 0087782-A1, published Apr. 8, 2010, filed Oct. 7, 2009, and entitled "CATHETER BALLOON HAVING STRETCHABLE INTEGRATED CIRCUITRY AND SENSOR ARRAY;"

U.S. Patent Application publication no. 2010 0116526-A1, published May 13, 2010, filed Nov. 12, 2009, and entitled "EXTREMELY STRETCHABLE ELECTRONICS;"

U.S. Patent Application publication no. 2010 0178722-A1, published Jul. 15, 2010, filed Jan. 12, 2010, and entitled "METHODS AND APPLICATIONS OF NON-PLANAR IMAGING ARRAYS;" and U.S. Patent Application publication no. 2010 027119-A1, published Oct. 28, 2010, filed Nov. 24, 2009, and entitled "SYSTEMS, DEVICES, AND METHODS UTILIZING STRETCHABLE ELECTRONICS TO MEASURE TIRE OR ROAD SURFACE CONDITIONS."

Kim, D. H. et al. (2010). Dissolvable films of silk fibroin for ultrathin conformal bio-integrated electronics. Nature Materials, 9, 511-517.

Omenetto, F. G. and D. L. Kaplan. (2008). A new route for silk. Nature Photonics, 2, 641-643.

Omenetto, F. G., Kaplan, D. L. (2010). New opportunities for an ancient material. Science, 329, 528-531.

Halsed, W. S. (1913). Ligature and suture material. Journal of the American Medical Association, 60, 1119-1126.

Masuhiro, T., Yoko, G., Masaobu, N., et al. (1994). Structural changes of silk fibroin membranes induced by immersion in methanol aqueous solutions. Journal of Polymer Science, 5, 961-968.

Lawrence, B. D., Cronin-Golomb, M., Georgakoudi, I., et al. (2008). Bioactive silk protein biomaterial systems for optical devices. Biomacromolecules, 9, 1214-1220.

Demura, M., Asakura, T. (1989). Immobilization of glucose oxidase with Bombyx mori silk fibroin by only stretching treatment and its application to glucose sensor. Biotechnololgy and Bioengineering, 33, 598-603.

Wang, X., Zhang, X., Castellot, J. et al. (2008). Controlled release from multilayer silk biomaterial coatings to modulate vascular cell responses. Biomaterials, 29, 894-903.

U.S. patent application Ser. No. 12/723,475 entitled "SYSTEMS, METHODS, AND DEVICES FOR SENSING AND TREATMENT HAVING STRETCHABLE INTEGRATED CIRCUITRY," filed Mar. 12, 2010.

U.S. patent application Ser. No. 12/686,076 entitled "Methods and Applications of Non-Planar Imaging Arrays," filed Jan. 12, 2010.

U.S. patent application Ser. No. 12/636,071 entitled "Systems, Methods, and Devices Using Stretchable or Flexible Electronics for Medical Applications," filed Dec. 11, 2009.

U.S. Patent Application publication no 2012-0065937-A1, published Mar. 15, 2012, and entitled "METHODS AND APPARATUS FOR MEASURING TECHNICAL PARAMETERS OF EQUIPMENT, TOOLS AND COMPONENTS VIA CONFORMAL ELECTRONICS."

U.S. patent application Ser. No. 12/616,922 entitled "Extremely Stretchable Electronics," filed Nov. 12, 2009.

U.S. patent application Ser. No. 12/575,008 entitled "Catheter Balloon Having Stretchable Integrated Circuitry and Sensor Array," filed on Oct. 7, 2009.

U.S. patent application Ser. No. 13/336,518 entitled "Systems, Methods, and Devices Having Stretchable Integrated Circuitry for Sensing and Delivering Therapy," filed Dec. 23, 2011.

U.S. patent application Ser. No. 13/843,873 entitled "STRAIN ISOLATION STRUCTURES FOR STRETCHABLE ELECTRONICS," filed Mar. 15, 2013.

U.S. patent application Ser. No. 13/843,880 entitled "STRAIN RELIEF STRUCTURES FOR STRETCHABLE INTERCONNECTS," filed Mar. 15, 2013.

It should be appreciated that all combinations of the foregoing concepts and additional concepts described in greater detail below (provided such concepts are not mutually inconsistent) are contemplated as being part of the inventive subject matter disclosed herein. It also should be appreciated that terminology explicitly employed herein that also may appear in any disclosure incorporated by reference should be accorded a meaning most consistent with the particular concepts disclosed herein.

BRIEF DESCRIPTION OF THE DRAWINGS

The skilled artisan will understand that the figures, described herein, are for illustration purposes only, and that the drawings are not intended to limit the scope of the disclosed teachings in any way. In some instances, various aspects or features may be shown exaggerated or enlarged to facilitate an understanding of the inventive concepts disclosed herein (the drawings are not necessarily to scale, emphasis instead being placed upon illustrating the principles of the teachings). In the drawings, like reference characters generally refer to like features, functionally similar and/or structurally similar elements throughout the various figures.

FIGS. 15A-15D show example device configurations according to the principles described herein.

FIGS. 16A-16C show example system configurations according to the principles described herein.

DETAILED DESCRIPTION

Figure 1:
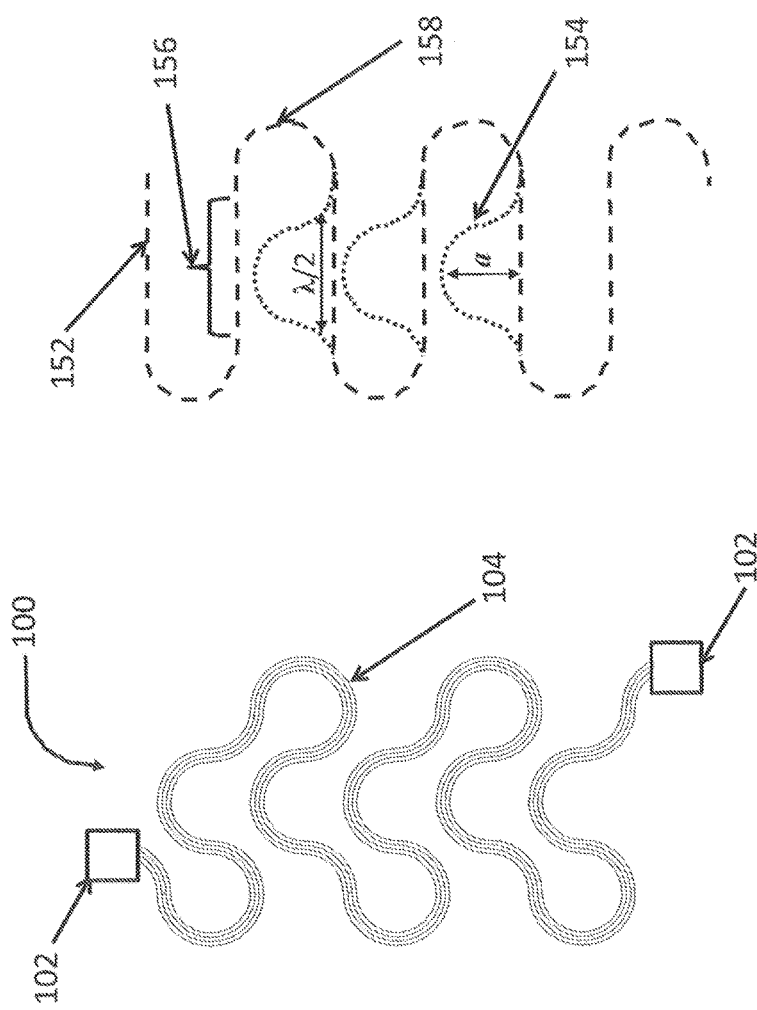
FIG. 1A shows an example stretchable device according to the principles described herein.
FIG. 1B shows an example of the composite configurations of the example interconnect of FIG. 1A, according to the principles described herein.

Following below are more detailed descriptions of various concepts related to, and embodiments of, inventive methods, apparatus and systems for monitoring hydration via conformal electronics. It should be appreciated that various concepts introduced above and discussed in greater detail below may be implemented in any of numerous ways, as the disclosed concepts are not limited to any particular manner of implementation. Examples of specific implementations and applications are provided primarily for illustrative purposes.

As used herein, the term "includes" means includes but is not limited to, the term "including" means including but not limited to. The term "based on" means based at least in part on.

With respect to substrates or other surfaces described herein in connection with various examples of the principles herein, any references to "top" surface and "bottom" surface are used primarily to indicate relative position, alignment and/or orientation of various elements/components with respect to the substrate and each other, and these terms do not necessarily indicate any particular frame of reference (e.g., a gravitational frame of reference). Thus, reference to a "bottom" of a substrate or a layer does not necessarily require that the indicated surface or layer be facing a ground surface. Similarly, terms such as "over," "under," "above," "beneath" and the like do not necessarily indicate any particular frame of reference, such as a gravitational frame of reference, but rather are used primarily to indicate relative position, alignment and/or orientation of various elements/components with respect to the substrate (or other surface) and each other. The terms "disposed on" "disposed in" and "disposed over" encompass the meaning of "embedded in," including "partially embedded in." In addition, reference to feature A being "disposed on," "disposed between," or "disposed over" feature B encompasses examples where feature A is in contact with feature B, as well as examples where other layers and/or other components are positioned between feature A and feature B.

Example systems, apparatus and methods described herein provide conformal electronics that present greater stretchability and flexibility than existing devices due to implementation of an example interconnect according to the principles described herein. In an example, the conformal electronics can be formed as stretchable electrical devices that include electrical contacts and at least one electrical interconnect electrically coupling the electrical contacts. In an example, the conformal electronics can be formed as stretchable devices that include a stretchable substrate and a stretchable electronic circuit disposed on a surface of the stretchable substrate. As a non-limiting example, the stretchable electronic circuit can include at least one discrete operative device and a stretchable interconnect coupled to the at least one discrete operative device. For example, the stretchable interconnect according to the principles herein can be implemented to couple a first discrete operative device to a second discrete operative device.

In any example herein, the example interconnect can be configured as a fractal serpentine interconnect.

In one non-limiting example implementation, the fractal serpentine interconnect can be configured to have a meander-shaped configuration that includes at least one nested serpentine-shaped feature.

In another the electrical interconnect non-limiting example implementation, the fractal serpentine interconnect can be configured to have a serpentine-in-serpentine ("SiS") configuration that includes a serpentine-shaped structure including at least one nested serpentine-shaped feature.

Any example fractal serpentine interconnect according to the principles herein can be formed as an electrically conductive interconnect. In other examples, the example fractal serpentine interconnect can be formed as a thermally conductive interconnect, or as a non-conductive interconnect formed from an electrically non-conductive material.

In any example implementation, a fractal serpentine interconnect according to the principles herein can be formed as bi-axial, extremely stretchable, high fill-factor interconnects. An example fractal serpentine interconnect can be configured as "fractal" serpentine structures built into a "base" overall meander-shaped structure (including a serpentine structure). In an example, the example fractal serpentine structures can be configured as a nested serpentine feature. An example fractal serpentine interconnect can be configured in such a way that the fractal features have multiple wavelengths, amplitudes, and are positioned in locations that allow the base serpentine interconnect or meander-shaped structure to be stretched in multiple directions, such as, e.g., the transversal direction. Due to the fractal serpentine design, the overall length of the interconnects according to the principles described herein (also referred to as fractal serpentine interconnects) is greater than that of other existing serpentine or meander-shaped structures. That is, if a fractal serpentine interconnect according to the principles herein were stretched and extended to the full length, the fractal serpentine interconnect would be longer in length than an interconnect having a solely meander shape (including a serpentine shape). Thus, the fractal serpentine interconnect configuration facilitates fitting a longer length of interconnect into effectively the same stretchable area. Thus, the fractal serpentine interconnect configurations according to the principles described herein present high fill factors and are extremely stretchable and flexible.

In example implementations, apparatus according to the principles described herein include devices based on conformal (e.g., stretchable, flexible and/or bendable) electronics that include the fractal serpentine interconnects.

In an example, the fractal serpentine interconnects can be formed from a conductive material or from a non-conductive material.

In an example, a system, apparatus and method is provided that is based on thin device islands, including integrated circuitry (IC) chips and/or stretchable interconnects that are embedded in a flexible polymer.

FIG. 1A shows an example stretchable device according to the principles described herein. The example stretchable device 100 includes contacts 102 and at least one interconnect 154 coupled to the contacts 102. In an example, contacts 102 can be electrical contacts, and the interconnect 154 can be an electrical interconnect that electrically couples the electrical contacts. In this example, the example interconnect 154 has a meander-shaped configuration that includes at least one nested serpentine-shaped feature.

FIG. 1B shows the composite configurations of the interconnect 154 of FIG. 1A. Interconnect 154 is comprised of a meander-shaped configuration 152 that includes several nested serpentine-shaped features 154. In this example, each nested serpentine-shaped features 154 is disposed at a portion 156 of each repeat loop of the meander-shaped configuration 152. In other examples, the nested serpentine-shaped feature 154 may be disposed at different portions of the meander-shaped configuration 152, such as but not limited to, at a tip 158 of a loop of the meander-shaped configuration 152. In other examples, the nested serpentine-shaped feature 154 may be disposed both at a position along a length of a loop (such as position 156) and at a tip of a loop (such as position 158). In some examples, the nested serpentine-shaped features 154 of an interconnect 154 may be configured with multiple differing wavelengths ($\lambda$) and/or differing amplitudes ($\alpha$).

Figure 2:
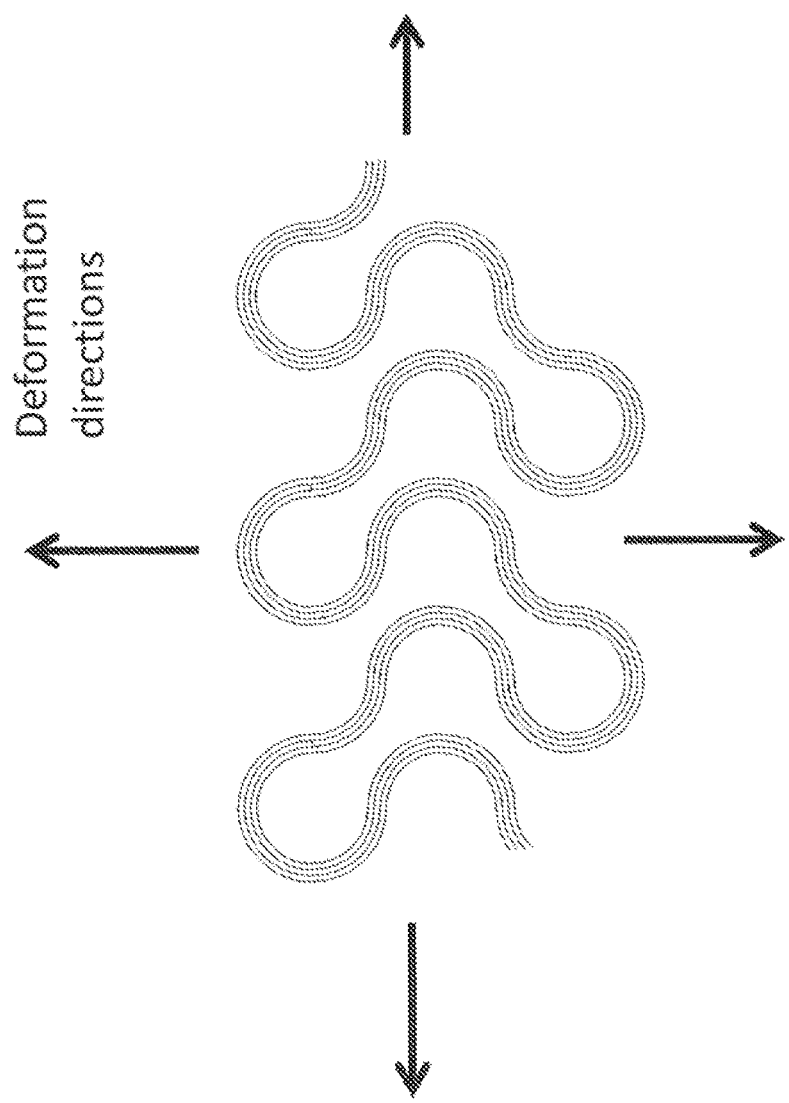
FIG. 2 shows an example of the deformation of an interconnect according to the principles described herein.

FIG. 2 shows an example of the stretching direction and expansion directions of an example fractal serpentine interconnect. Any example interconnect described herein can be subjected to several different directions of deformation. According to the principles herein, the nested serpentine-shaped features are disposed at portions of the meander-shaped configuration such that the interconnect can be stretched in a bi-axial direction or multiple directions, such as but not limited to a transversal direction.

Figure 3:
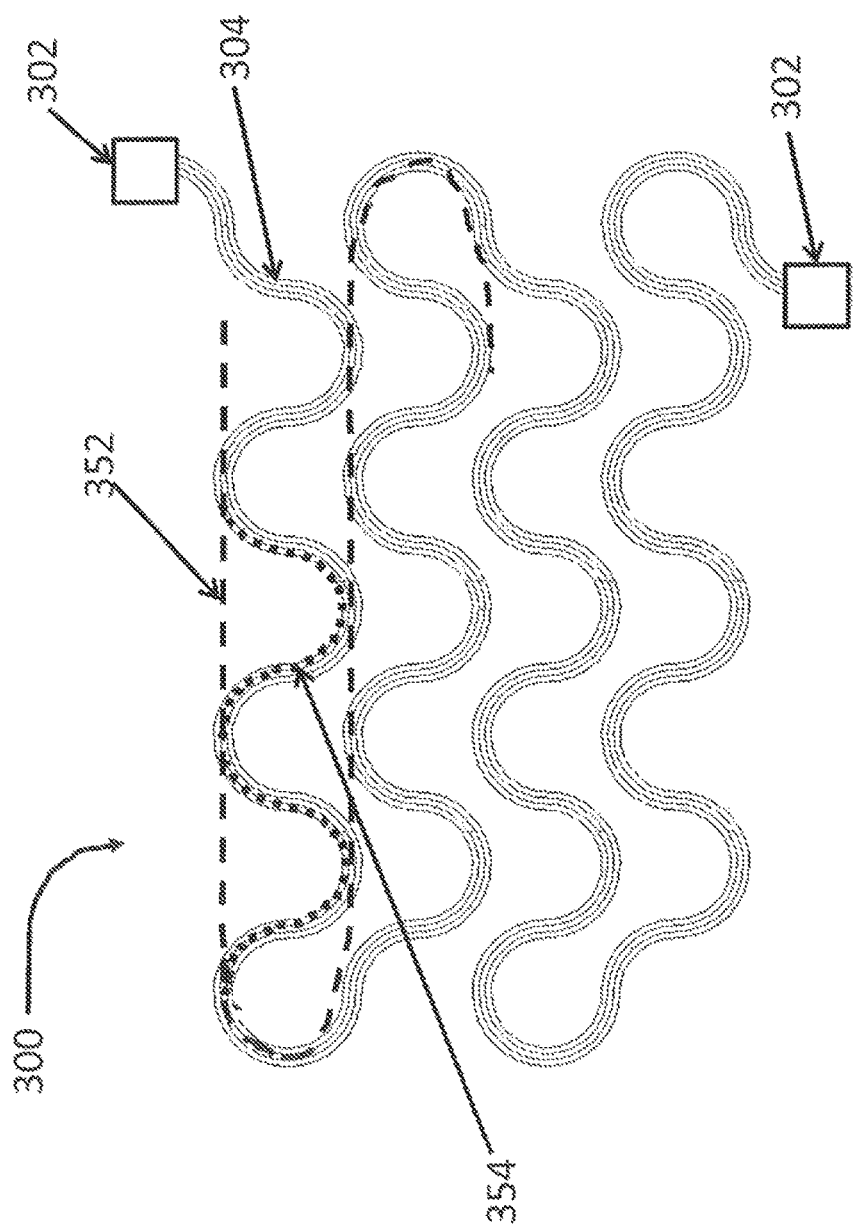
FIG. 3 is an example stretchable device according to the principles described herein.

FIG. 3 shows another example stretchable device according to the principles described herein. The example stretchable device 300 includes contacts 302 and at least one interconnect 304 coupled to the contacts 302. In an example, contacts 302 can be electrical contacts, and the interconnect 304 can be an electrical interconnect that electrically couples the electrical contacts. In this example, the example interconnect 304 has a meander-shaped configuration 352 that includes several nested serpentine-shaped features 354. The nested serpentine-shaped features 354 are disposed at regions along each repeat loop of the meander-shaped configuration 352. In some examples, the nested serpentine-shaped features 354 of an interconnect 304 may be configured with multiple differing wavelengths and/or differing amplitudes.

Figure 4:
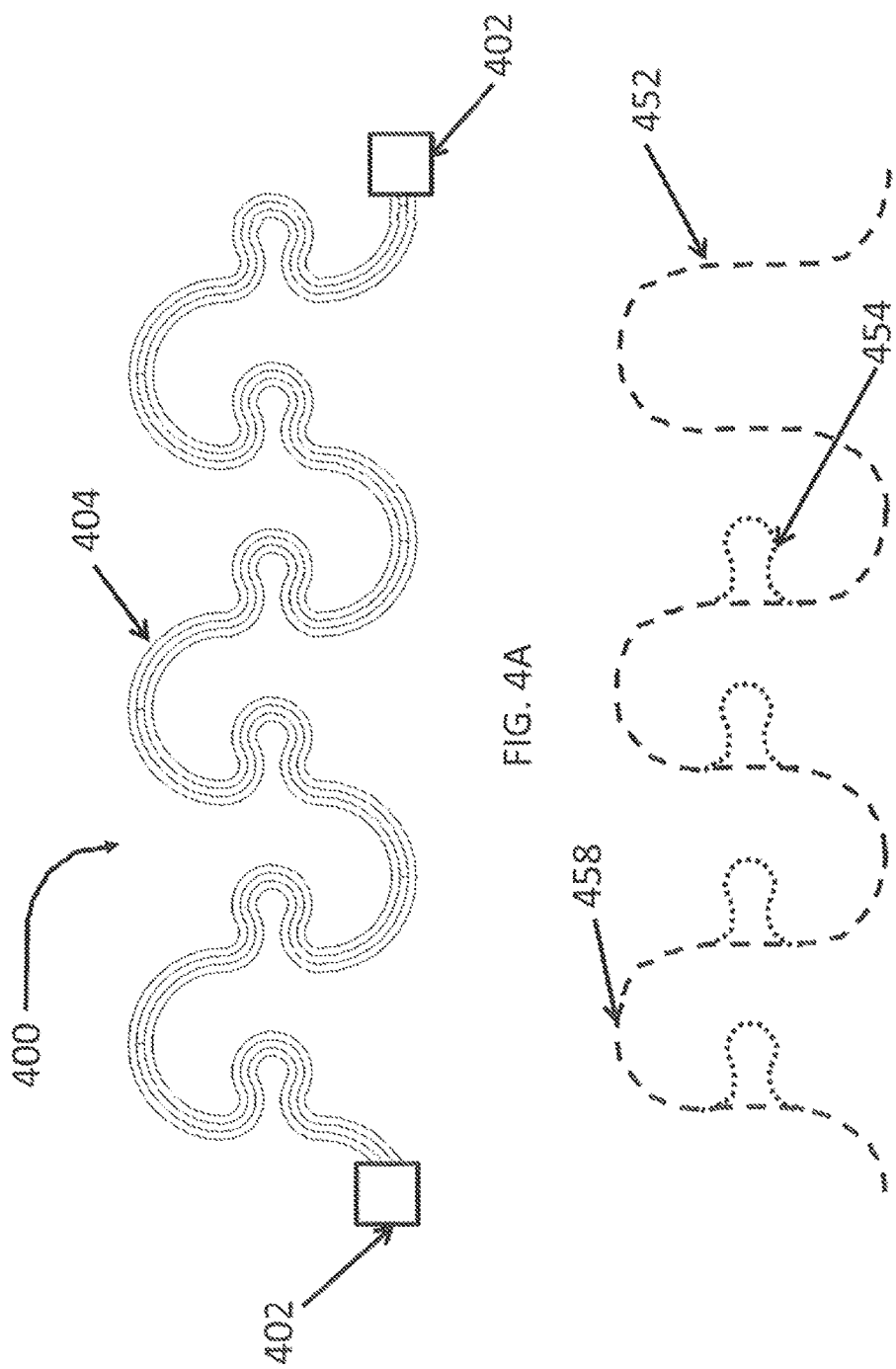
FIG. 4A shows another example stretchable device according to the principles described herein.
FIG. 4B shows an example of the composite configurations of the example interconnect of FIG. 4A, according to the principles described herein.

FIG. 4A shows another example stretchable device according to the principles described herein. The example stretchable device 400 includes contacts 402 and at least one interconnect 404 coupled to the contacts 402. In an example, contacts 402 can be electrical contacts, and the interconnect 404 can be an electrical interconnect that electrically couples the electrical contacts. FIG. 4B shows the composite configurations of the interconnect 404 of FIG. 4A. Example interconnect 404 has a meander-shaped configuration 452 that includes several nested serpentine-shaped features 454. The nested serpentine-shaped features 454 are disposed at regions along each repeat loop of the meander-shaped configuration 452. In other examples, the nested serpentine-shaped feature 454 may be disposed at different portions of the meander-shaped configuration 452, such as but not limited to, at a tip 458 of a loop of the meander-shaped configuration 452. In other examples, the nested serpentine-shaped feature 454 may be disposed both at a position along a length of a loop and at a tip of a loop (such as position 458). In some examples, the nested serpentine-shaped features 454 of an interconnect 404 may be configured with multiple differing wavelengths and/or differing amplitudes.

Figure 5:
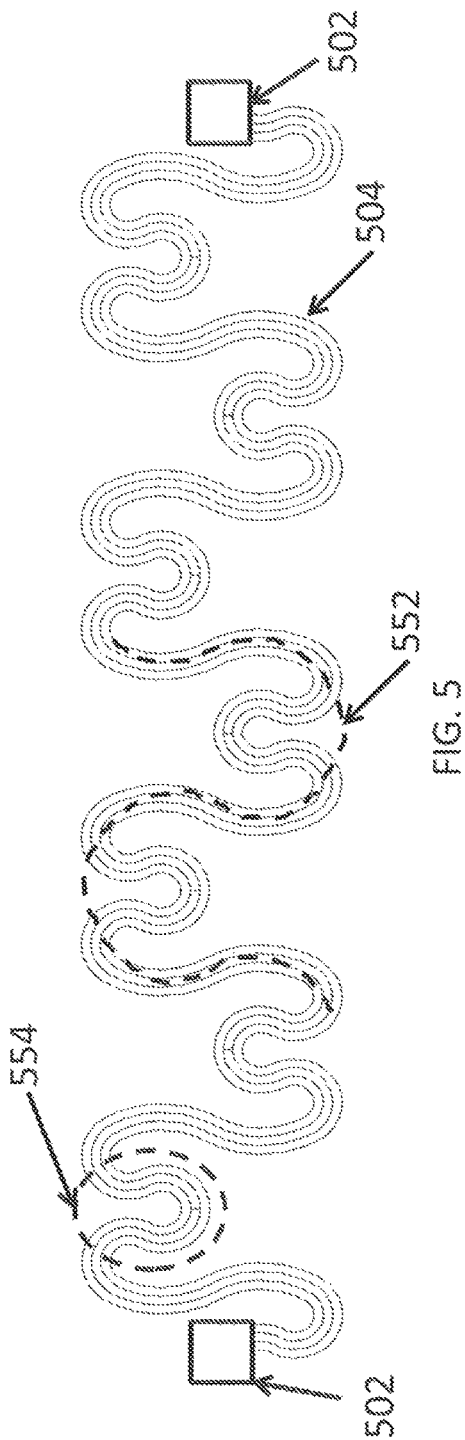
FIG. 5 shows an example stretchable device according to the principles described herein.
Figure 6:
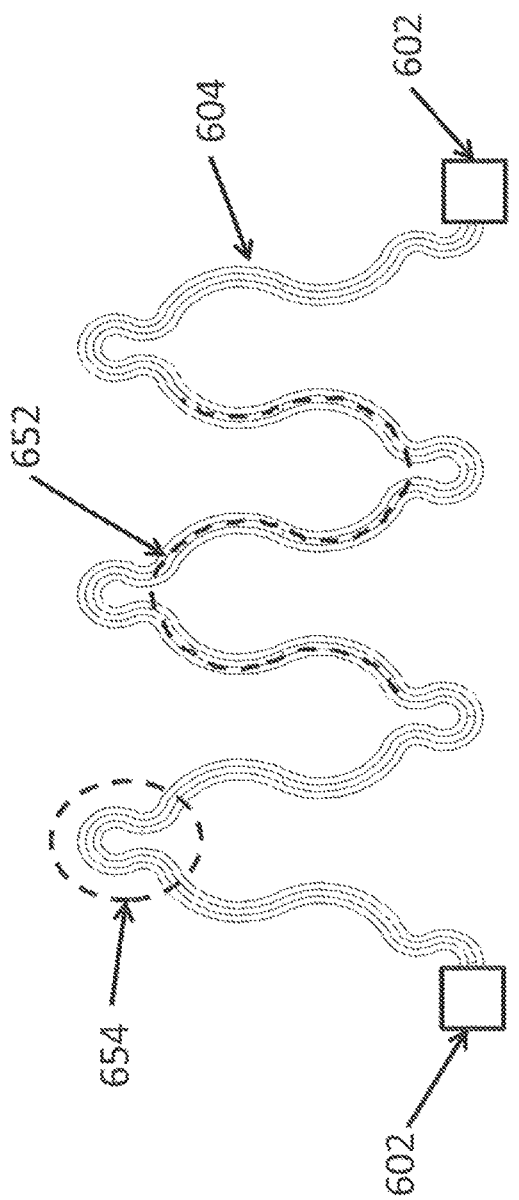
FIG. 6 shows an example stretchable device according to the principles described herein.

FIGS. 5 and 6 show other example stretchable devices according to the principles described herein that include interconnects having a meander-shaped configuration including at least one nested serpentine-shaped feature. In the examples of FIGS. 5 and 6, the meander-shaped configuration is serpentine-shaped, such that the interconnect has a serpentine-in-serpentine (SiS) configuration. The example stretchable device of FIG. 5 includes contacts 502 and at least one interconnect 504 coupled to the contacts 502. Example interconnect 504 has a serpentine-shaped structure 552 that includes several nested serpentine-shaped features 554. The nested serpentine-shaped features 554 are disposed at the tips of each repeat loop of the serpentine-shaped structure 552. In this example, the nested serpentine-shaped features 554 are oriented towards the midpoint of each loop. The example stretchable device of FIG. 6 includes contacts 602 and at least one interconnect 604 coupled to the contacts 602. Example interconnect 604 has a serpentine-shaped structure 652 that includes several nested serpentine-shaped features 654. The nested serpentine-shaped features 654 are disposed at the tips of each repeat loop of the serpentine-shaped structure 652. In this example, the nested serpentine-shaped features 654 are oriented outwards from each loop.

Example contacts 502 and 602 can be configured as electrical contacts, and the interconnects 504 and 604 can be electrical interconnects that electrically couples the respective electrical contacts. In some examples, the nested serpentine-shaped feature 554 or 654 may be disposed at different portions of the serpentine-shaped structure 552 or 652, such as but not limited to, along a portion of a length of a loop. In other examples, the nested serpentine-shaped feature 554 or 654 may be disposed both at a position along a length of a loop and at a tip of a loop. In some examples, the nested serpentine-shaped features 554 and 654 of an interconnect 504 and 604, respectively, may be configured with multiple differing wavelengths and/or differing amplitudes.

Figure 7:
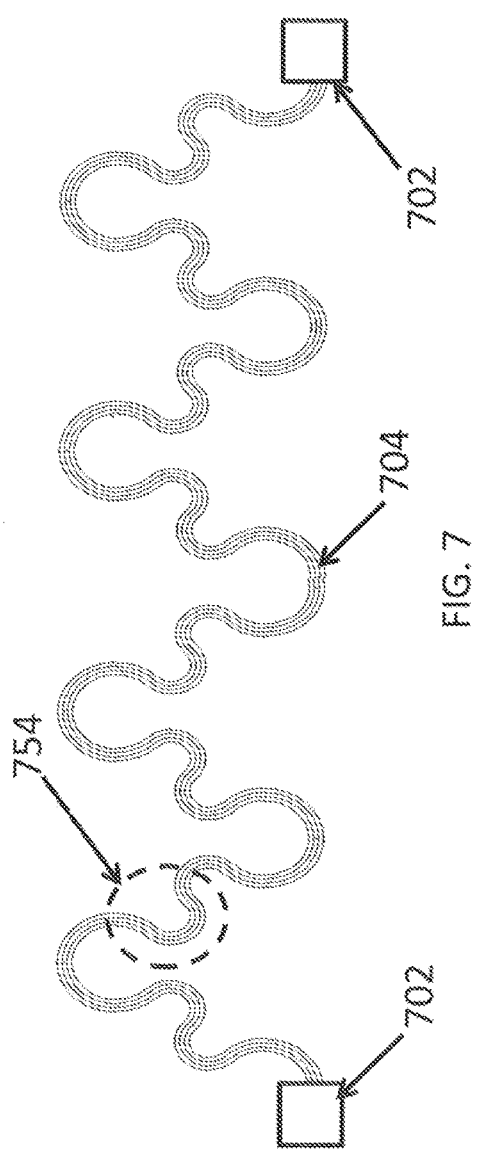
FIG. 7 shows an example stretchable device according to the principles described herein.
Figure 8:
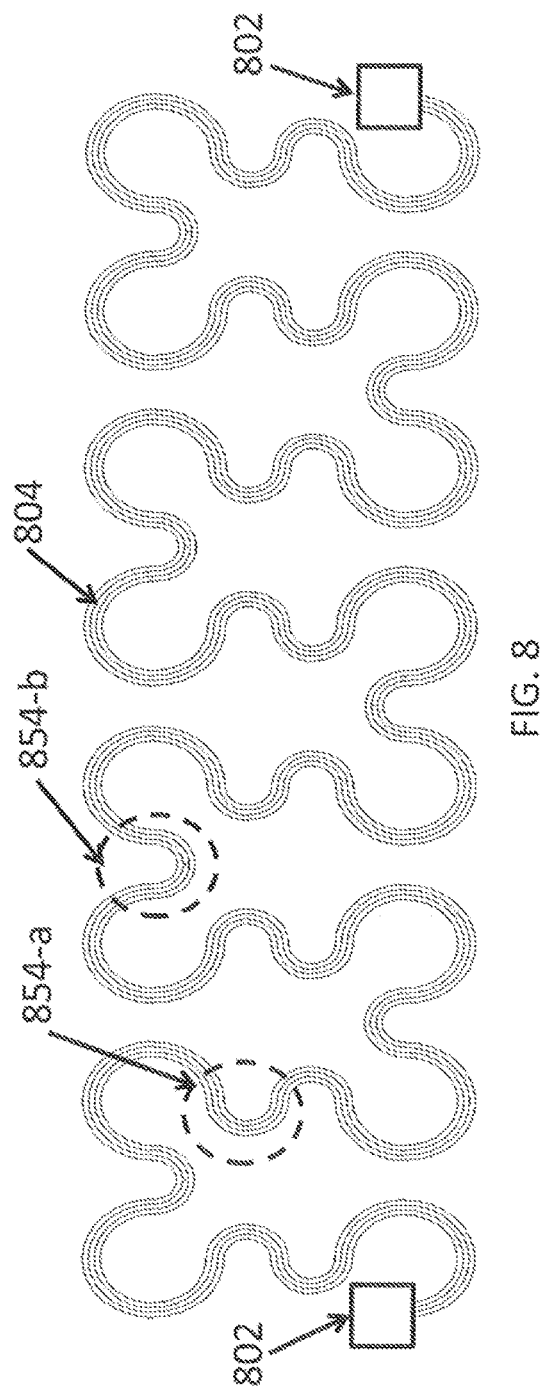
FIG. 8 shows an example stretchable device according to the principles described herein.

FIGS. 7 and 8 show other example stretchable devices according to the principles described herein that include interconnects having a meander-shaped configuration including nested serpentine-shaped features. The example stretchable device of FIG. 7 includes contacts 702 and at least one interconnect 704 coupled to the contacts 702. Example interconnect 704 has a meander-shaped configuration 752 that includes several nested serpentine-shaped features 754. The example stretchable device of FIG. 8 includes contacts 802 and at least one interconnect 804 coupled to the contacts 802. Example interconnect 804 has a meander-shaped configuration 852 that includes several nested serpentine-shaped features 854-a and 854-b. The nested serpentine-shaped features 854-a are disposed along a length of each repeat loop of the meander-shaped configuration 852, while nested serpentine-shaped features 854-b are disposed at the tips of each repeat loop of the meander-shaped configuration 852. Example contacts 702 and 702 can be configured as electrical contacts, and the interconnects 704 and 804 can be electrical interconnects that electrically couples the respective electrical contacts. In some examples, the nested serpentine-shaped feature 754 or 854 may be disposed at different portions of the serpentine-shaped structure 752 or 852, such as but not limited to, along a portion of a length of a loop. In other examples, the nested serpentine-shaped feature 754 or 854 may be disposed both at a position along a length of a loop and at a tip of a loop. In some examples, the nested serpentine-shaped features 754 and 854 interconnect 704 and 804, respectively, may be configured with multiple differing wavelengths and/or differing amplitudes.

Figure 9A:
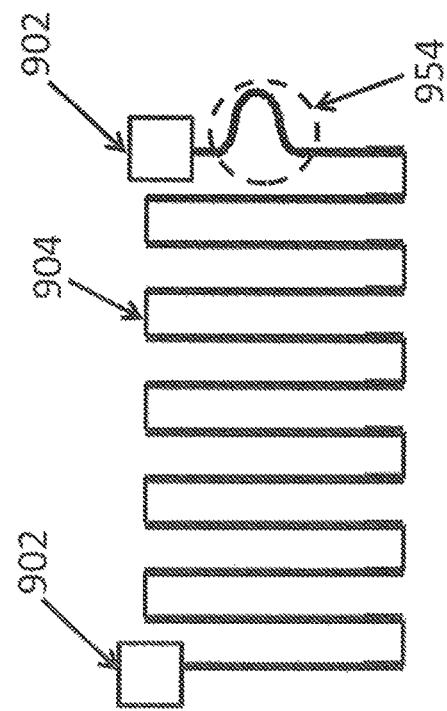
FIGS. 9A and 9B show other example interconnects according to the principles described herein.
Figure 9B:
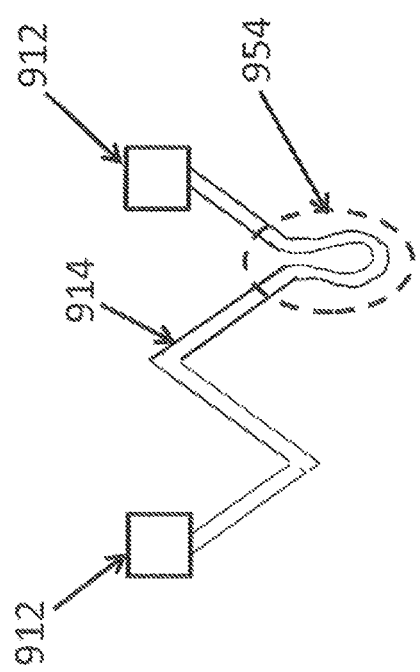

FIGS. 9A and 9B show other example interconnects that can be implemented based on differing types of meander-shaped configurations, according to the principles described herein. In the example of FIG. 9A, the meander-shaped configuration is a boustrophedonic-shaped structure. The example stretchable device of FIG. 9A includes contacts 902 and an interconnect 904 coupled to the contacts 902, where the example interconnect 904 has a boustrophedonic-shaped structure that includes at least one nested serpentine-shaped feature 954. In the example of FIG. 9B, the meander-shaped configuration is a zig-zag-shaped structure. The example stretchable device of FIG. 9B includes contacts 912 and an interconnect 914 coupled to the contacts 912, where the example interconnect 914 has a zig-zag-shaped structure that includes at least one nested serpentine-shaped feature 954.

In other examples, the interconnect can have any other meander-shaped configuration in the art. For example, the meander-shaped configuration can be configured to have any number of linear or non-linear structure, including a corrugated or rippled structure, a helical structure, or any other configuration of that provides a flexible and/or stretchable interconnect.

Figure 10:
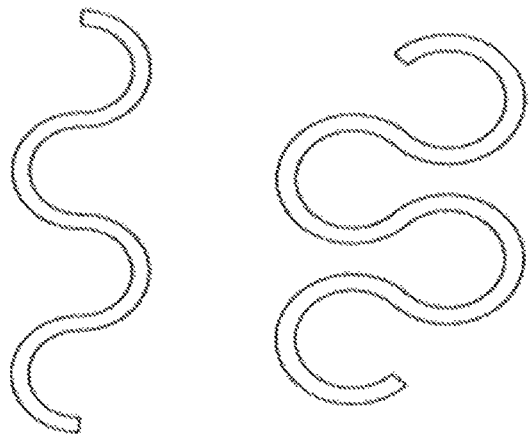
FIGS. 10A and 10B show examples of shaped of serpentine-shaped features according to the principles described herein.

FIGS. 10A and 10B show other non-limiting examples of serpentine shapes that the can be implemented as nested serpentine-shaped features, according to the principles described herein. As shown in FIGS. 10A and 10B, the nested serpentine-shaped feature can be modeled as a series of circular arcs. The turning angle of the arcs in the example of FIG. 10A are smaller than the turning angle of the arcs in the example of FIG. 10B. Therefore, the arcs of the example serpentine structure of FIG. 10B are more circular than the arcs of the example serpentine structure of FIG. 10A.

In any example implementation, a stretchable device can include electrical contacts and at least one interconnect disposed on a flexible and/or stretchable substrate. In an example, the flexible and/or stretchable substrate can be an elastomeric substrate. In an example, the electrical contacts can be in physical communication with the surface of the flexible and/or stretchable substrate and the interconnect is not in physical communication with the flexible and/or stretchable substrate.

In any example implementation, the electrical contacts can be in communication with a semiconductor circuit.

In any example implementation, the electrical contacts can be in communication with at least one device component in communication with at least one electrical contact, and wherein the at least one device component is an electronic device component, an optical device component, an optoelectronic device component, a mechanical device component, a microelectromechanical device component, a nanoelectromechanical device component, a microfluidic device component or a thermal device.

In any of the examples described herein, the electrically conductive material (such as but not limited to the material of the electrical interconnect and/or the electrical contact) can be, but is not limited to, a metal, a metal alloy, a conductive polymer, or other conductive material. In an example, the metal or metal alloy of the coating may include but not limited to aluminum, stainless steel, or a transition metal, and any applicable metal alloy, including alloys with carbon. Non-limiting examples of the transition metal include copper, silver, gold, platinum, zinc, nickel, titanium, chromium, or palladium, or any combination thereof. In other non-limiting examples, suitable conductive materials may include a semiconductor-based conductive material, including a silicon-based conductive material, indium tin oxide or other transparent conductive oxide, or Group III-IV conductor (including GaAs). The semiconductor-based conductive material may be doped.

In any of the example structures described herein, the interconnects can have a thickness of about 0.1 µm, about 0.3 µm, about 0.5 µm, about 0.8 µm, about 1 µm, about 1.5 µm, about 2 µm, about 5 µm, about 9 µm, about 12 µm, about 25 µm, about 50 µm, about 75 µm, about 100 µm, or greater.

In an example system, apparatus and method, the interconnects can be formed from a non-conductive material and can be used to provide some mechanical stability and/or mechanical stretchability between components of the conformal electronics (e.g., between device components). As a non-limiting example, the non-conductive material can be formed based on a polyimide.

In any of the example devices according to the principles described herein, the non-conductive material (such as but not limited to the material of a stretchable interconnect) can be formed from any material having elastic properties. For example, the non-conductive material can be formed from a polymer or polymeric material. Non-limiting examples of applicable polymers or polymeric materials include, but are not limited to, a polyimide, a polyethylene terephthalate (PET), a silicone, or a polyurethane. Other non-limiting examples of applicable polymers or polymeric materials include plastics, elastomers, thermoplastic elastomers, elastoplastics, thermostats, thermoplastics, acrylates, acetal polymers, biodegradable polymers, cellulosic polymers, fluoropolymers, nylons, polyacrylonitrile polymers, polyamide-imide polymers, polyarylates, polybenzimidazole, polybutylene, polycarbonate, polyesters, polyetherimide, polyethylene, polyethylene copolymers and modified polyethylenes, polyketones, poly(methyl methacrylate, polymethylpentene, polyphenylene oxides and polyphenylene sulfides, polyphthalamide, polypropylene, polyurethanes, styrenic resins, sulphone based resins, vinyl-based resins, or any combinations of these materials. In an example, a polymer or polymeric material herein can be a DYMAX® polymer (Dymax Corporation, Torrington, Conn.). or other UV curable polymer, or a silicone such as but not limited to ECOFLEX® (BASF, Florham Park, N.J.).

In any example herein, the non-conductive material can have a thickness of about 0.1 µm, about 0.3 µm, about 0.5 µm, about 0.8 µm, about 1 µm, about 1.5 µm, about 2 µm or greater. In other examples herein, the non-conductive material can have a thickness of about 10 µm, about 20 µm, about 25 µm, about 50 µm, about 75 µm, about 100 µm, about 125 µm, about 150 µm, about 200 µm or greater.

Figure 11C:
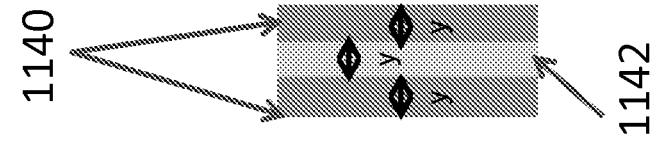
FIGS. 11A-11C shows examples of interconnects according to the principles described herein.
Figure 11B:
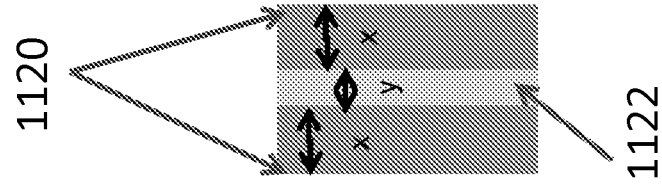
Figure 11A:
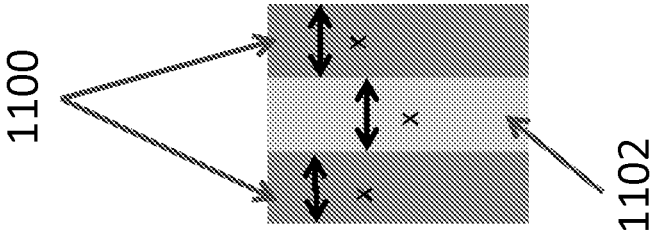

In an example system, apparatus and method, the interconnects can be formed from an electrically conductive material that is covered or coated at least in part by a non-conductive material. In an example implementation where the conductive interconnect includes a coating of a non-conductive material, the dimensions of the interconnects can be defined based on the thickness of the conductive portion of the interconnect versus the thickness of the non-conductive coating material, also referred to as the "trace and space". FIGS. 11A-11C shows variations of the top-view cross-sections of interconnects including a conductive portion 1102, 1122, 1142 and a non-conductive coating 1100, 1120, 1140. In the examples of FIGS. 11A and 11C, the conductive portion and the non-conductive portion have approximately the same width. In the example of FIG. 11B, the non-conductive portion has a greater width than the conductive portion.

In an example implementation illustrated in FIGS. 11A-11C, notation "x" can represent a dimension of about 75 µm and notation "y" can represent a dimension of about 25 µm. In an example, the dimensions of FIG. 11A can be used where the thickness of the conductive portion is about 5 µm to about 18 µm thick. When the thickness of conductive portion is increased, the thickness of the non-conductive portion may be reduced to maintain the same interconnect thickness.

Non-limiting example processes that can be used for generating the interconnects include an etching process, a metal deposition process, or other wafer-based fabrication process. A metal deposition process may be used to provide interconnects with greater thicknesses. A wafer-based process may be used to provide interconnects with finer lateral features. In this example, any interconnect or other structure made using a wafer-based fabrication process may be released from the wafer substrate prior to further processing.

In an example system, apparatus and method, sensors and other electronics are described herein that can include one or more of any of the fractal serpentine interconnects according to the principles described herein.

In an example system, apparatus and method, the interconnects can be formed from an electrically and/or thermally conductive material and can be used to provide electrical and/or thermal communication between components of the conformal electronics, e.g., between discrete operative device components. In any of the example devices according to the principles described herein, at least a portion of an example interconnect can be formed from an electrically conductive material.

An example stretchable device according to the principles described herein can include an example stretchable and/or flexible substrate, and an example stretchable electronic circuit disposed on a surface of the stretchable and/or flexible substrate. In an example, the stretchable electronic circuit can include at least one discrete operative device coupled to a stretchable interconnect that has a meander-shaped configuration including at least one nested serpentine-shaped feature. For example, the stretchable electronic circuit can include two discrete operative devices and a stretchable interconnect coupled to the discrete operative devices, where the stretchable interconnect has a meander-shaped configuration including at least one nested serpentine-shaped feature.

Figure 12:
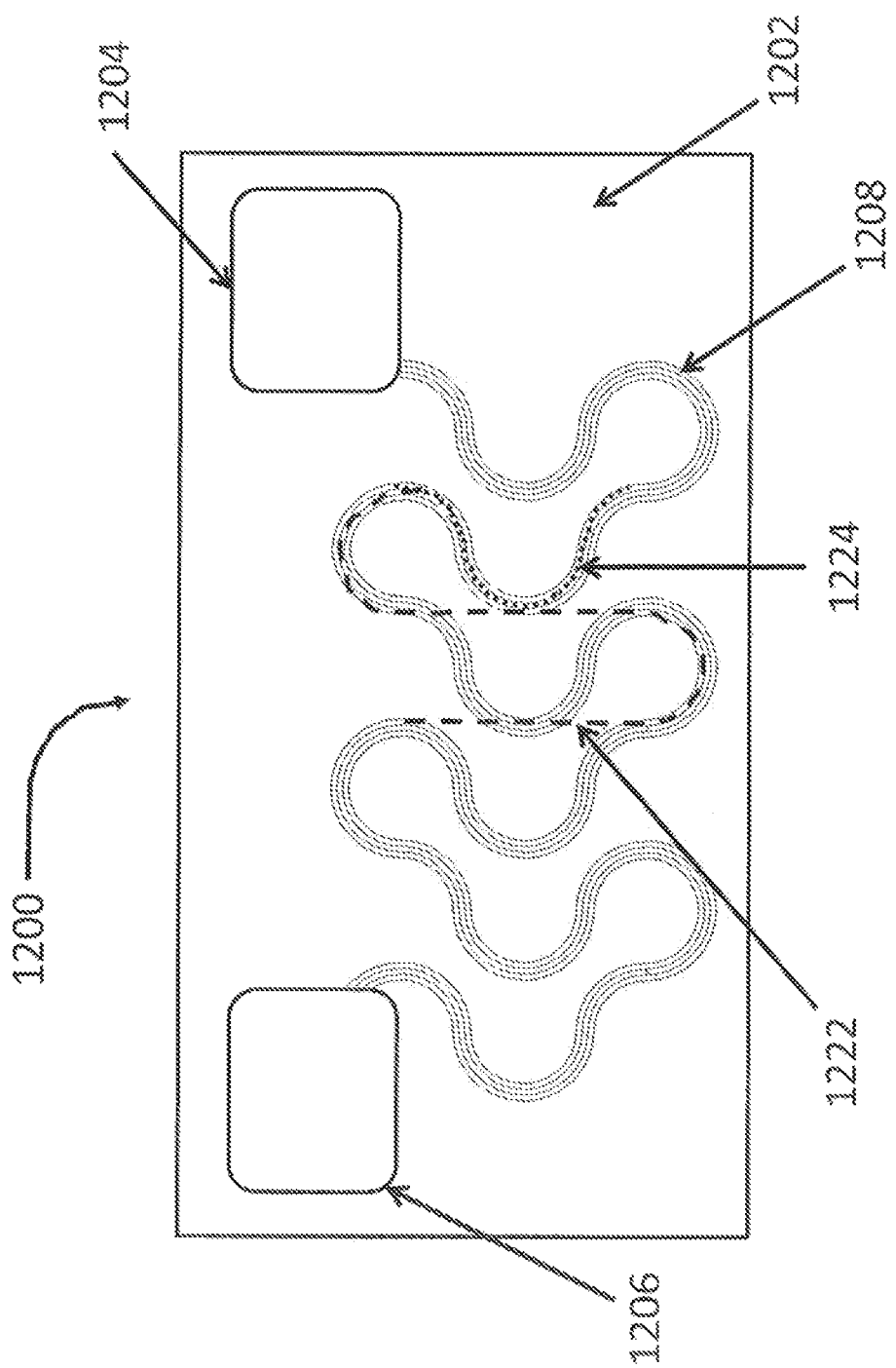
FIG. 12 shows an example stretchable device according to the principles described herein.

FIG. 12 shows an example stretchable device 1200 that includes an example stretchable and/or flexible substrate 1202, and an example stretchable electronic circuit disposed on a surface of the stretchable and/or flexible substrate 1202. In an example, the stretchable electronic circuit includes two discrete operative devices 1204, 1206 and a stretchable interconnect 1208 coupled to the discrete operative devices 1204, 1206. As shown in FIG. 12, the stretchable interconnect can have a meander-shaped configuration 1222 including at least one nested serpentine-shaped feature 1224. In different examples, the stretchable interconnect can be any interconnect according to any of the principles described herein, including the interconnect of any of FIGS. 1A through 10. The description of material composition, dimensions, and properties of any interconnect described herein, including the interconnects of any of FIGS. 1A through 10, apply to the stretchable interconnect of 1208.

In any example implementation, one or more of the discrete operative devices can include a metal contact. The stretchable interconnect can be electrically coupled to the contact.

In any example implementation, the stretchable interconnect and one or more of the discrete operative devices can be fabricated from the same material, such as but not limited to a semiconductor material.

In any example implementation, the stretchable interconnect can be made from a semiconductor material. The discrete operative device is formed from a different semiconductor material than the stretchable interconnect.

In any example implementation, the stretchable interconnect can be made from a single crystal semiconductor material.

In any example implementation, the one or more discrete operative devices can be in physical communication with the surface of a stretchable and/or flexible substrate, and the stretchable interconnect is not in physical communication with the surface of the flexible and/or stretchable substrate.

In any example herein, the discrete operative device can be a semiconductor device. For example, the discrete operative device can be one or more of an electronic device, an optical device, an opto-electronic device, a mechanical device, a microelectromechanical device, a nanoelectromechanical device, a microfluidic device, a sensor, a light-emitting device, or a thermal device.

For example, the discrete operative device can include one or more of a photodetector, a photodiode array, a display, a light-emitting device, a photovoltaic device, a sensor array, a light-emitting diode, a semiconductor laser, an optical imaging system, a transistor, a microprocessor, an integrated circuit, or any combination of thereof.

In an example, a conformal electronic structure is provided that includes a fractal serpentine interconnect in electrical communication with at least one device component. The fractal serpentine interconnects and at least one device component can be disposed on a portion of a supporting surface of a flexible and/or a stretchable substrate.

In a non-limiting example, the flexible substrate can be a polymer. For example, the flexible substrate can be, but is not limited to, an elastomer, a polyimide, a foil, paper, fabric, or other flexible material. In another example, the flexible substrate can be a stretchable substrate.

In another example, a conformal electronic structure is provided that includes at least one device component and at least two fractal serpentine interconnects, each of the at least two fractal serpentine interconnects being in electrical communication with the at least one device component.

In an example system, apparatus and method herein, a fully conformal electronic device is provided that includes one or more of the fractal serpentine interconnects. The fully conformal electronic device can be placed on, including being attached on, a variety of surface profiles, with minimal to no effect on the functionality of the conformal electronic device sensor. As a non-limiting example, the conformal device can be a sensor.

In an example, a stretchable device according to the principles described herein can be configured as a sensor. A portion of the example sensor can be formed with a fractal serpentine interconnect that maintains mechanical stability during deformation and/or stretching of the sensor. For example, the fractal serpentine interconnect can be formed at least in part from a non-conductive material that is stretchable. Components of the example sensors can be linked by one or more of the fractal serpentine interconnect to provide the mechanical stability during deformation and/or stretching of the sensor.

In a non-limiting example, a stretchable device according to the principles described herein can be formed as a two-dimensional device. The discrete operative device components can include one or more materials such as a metal, a semiconductor, an insulator, a piezoelectric material, a ferroelectric material, a magnetostrictive material, an electrostrictive material, a superconductor, a ferromagnetic material, or a thermoelectric material.

Figure 13A:
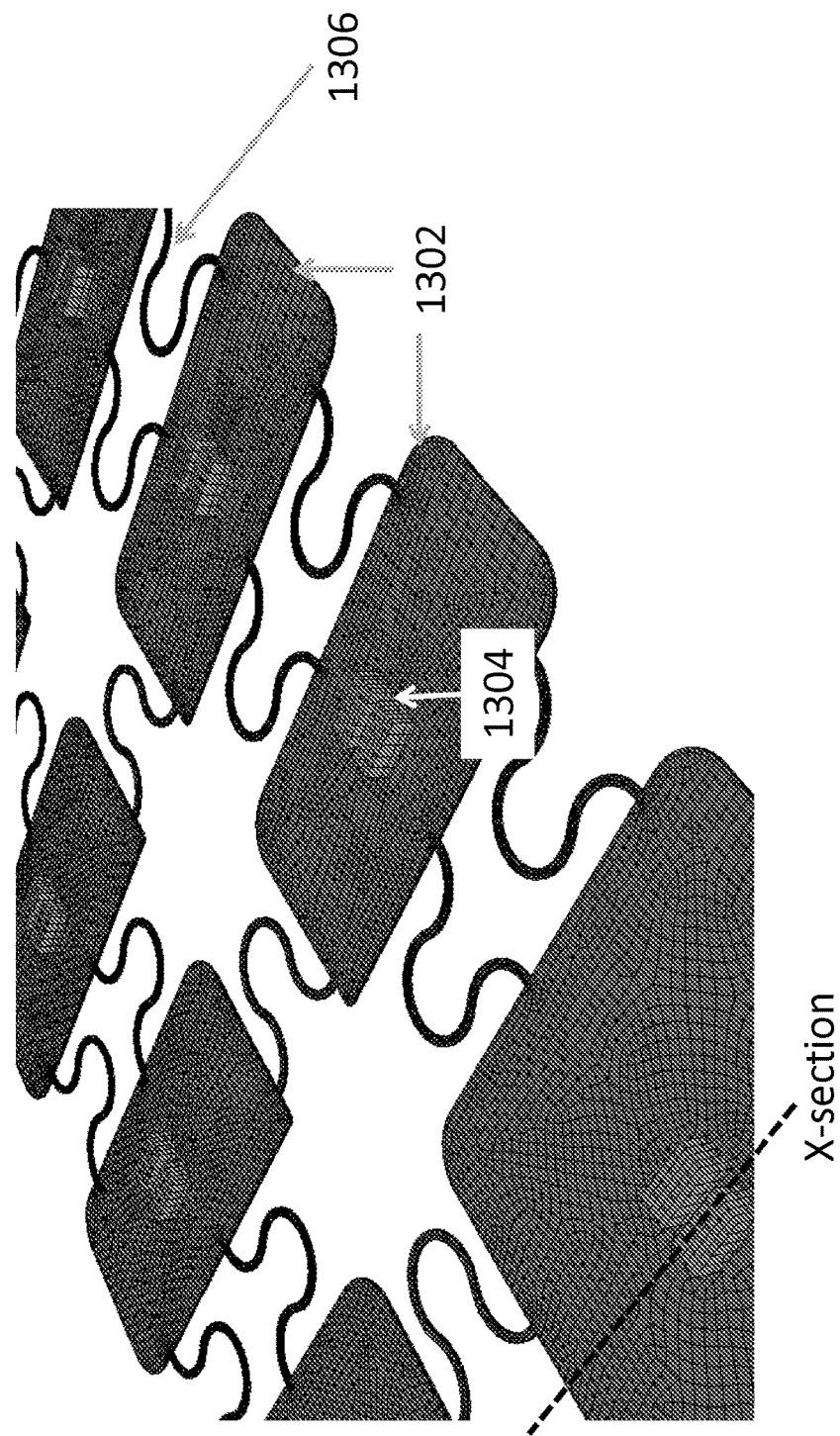
FIG. 13A shows an example configuration of interconnects and device islands according to the principles described herein.
Figure 13B:
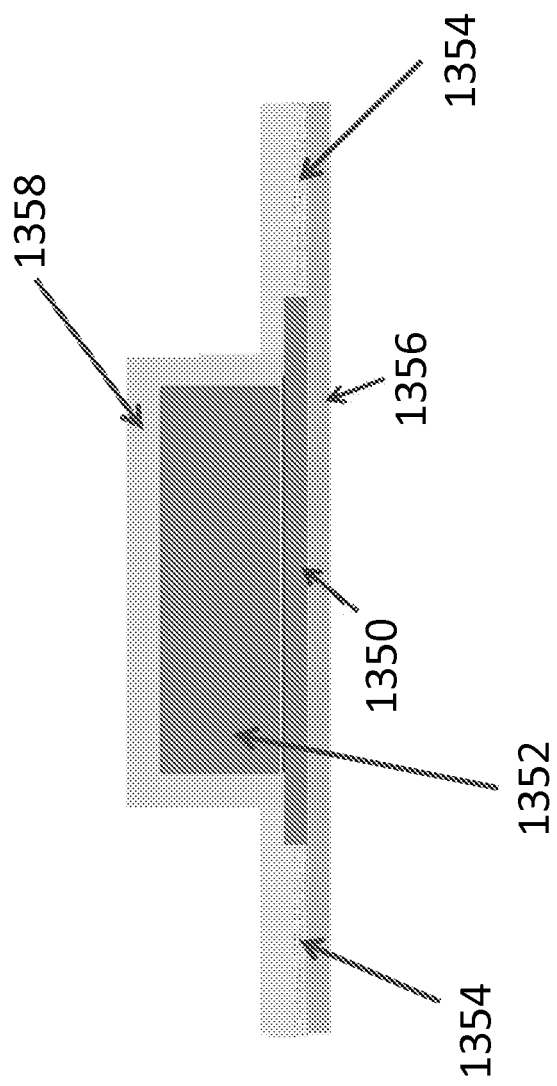
FIG. 13B shows an example cross-section of a portion of the interconnects and device islands of FIG. 13A according to the principles described herein.

In a non-limiting example stretchable device, at least one of the discrete operative components can be disposed on a device island, with the interconnect being coupled to the discrete operative component via the device island. FIGS. 13A-13B show an example of a configuration of interconnects disposed between, and coupled to, spaced apart device islands. As shown in FIG. 13A, the stretchable device can include a plurality of device islands 1302 arranged co-planar plane relative to each other, each of the device islands including one or more discrete operative device components 1304. A plurality of interconnects 1306 can be used to couple adjacent device islands, or to couple conductive contacts to device islands. While the example of FIG. 13A shows serpentine-shaped interconnects, one or more of the interconnects 1306 can be configured as a meander-shaped configuration including at least one nested serpentine-shaped feature according to the principles described herein. The resulting example stretchable device would have significantly greater flexibility, stretchability, and robustness to multi-axial deformations based on the greater stretchability of the fractal serpentine interconnect. In the example of FIG. 13A, two interconnects 1306 are used to couple device islands in each row or to couple contacts to the device islands; at least one interconnect 1306 couples adjacent device islands across the two rows.

In other example implementations, the device islands and/or the interconnects can be disposed in a three-dimensional arrangement. For example, the device islands and/or the interconnects the interconnects can be arranged in a single layer or in multiple layers (e.g., two or more layers). In an example, two or more interconnects between device islands can be disposed in a co-planar, substantially parallel arrangement. Any multiple-layered portion of an example structure can be arranged in a staggered arrangement, a stacking arrangement, or a randomized arrangement. That is, the interconnects can be multiple layer stacking, or can be placed in a coplanar parallel arrangement. In various examples, the components can be oriented in differing directions in each stacked layer, and/or each layer of the stacked layers can include differing numbers of device islands or interconnects. In other examples, at least a portion of the device islands and the interconnects of a structure can be disposed in a substantially curved arrangement.

FIG. 13B shows a cross-section through line "X-section" through the non-limiting example stretchable device of FIG. 13A. The stretchable device includes base plate 1350, a discrete operative electronic device component 1352 disposed over the base plate 1350, and interconnects 1354 coupled to a portion of the base plate 1350. The base plate is 1350 is disposed over a substrate 1356. The example stretchable device can include an encapsulant 1358 disposed over at least a portion of the discrete operative device 1352 and/or the interconnect 1354. The encapsulant can be formed from any polymer or polymeric material described herein.

In an example, the substrate 1356 can be a stretchable and/or flexible substrate. The substrate can be formed from any polymer or polymeric material described herein.

In an example, the base plate 1350 includes a polyimide layer (PI). For example, the base plate 135 can be about 50 µm thick. In any other example according to the principles herein, the example base plate can have any other dimensions or material compositions that provides for proper functioning of the overall conformal device as a conformal sensor system as described herein.

The base plate 1350 may include a contact formed from a conductive material that can serve as an electrical contact to the discrete operative electronic device component 1352 and/or the interconnect 1354. In an example, the contact can be copper (Cu) having a thickness of about 0.5 µm Cu.

Figure 14:
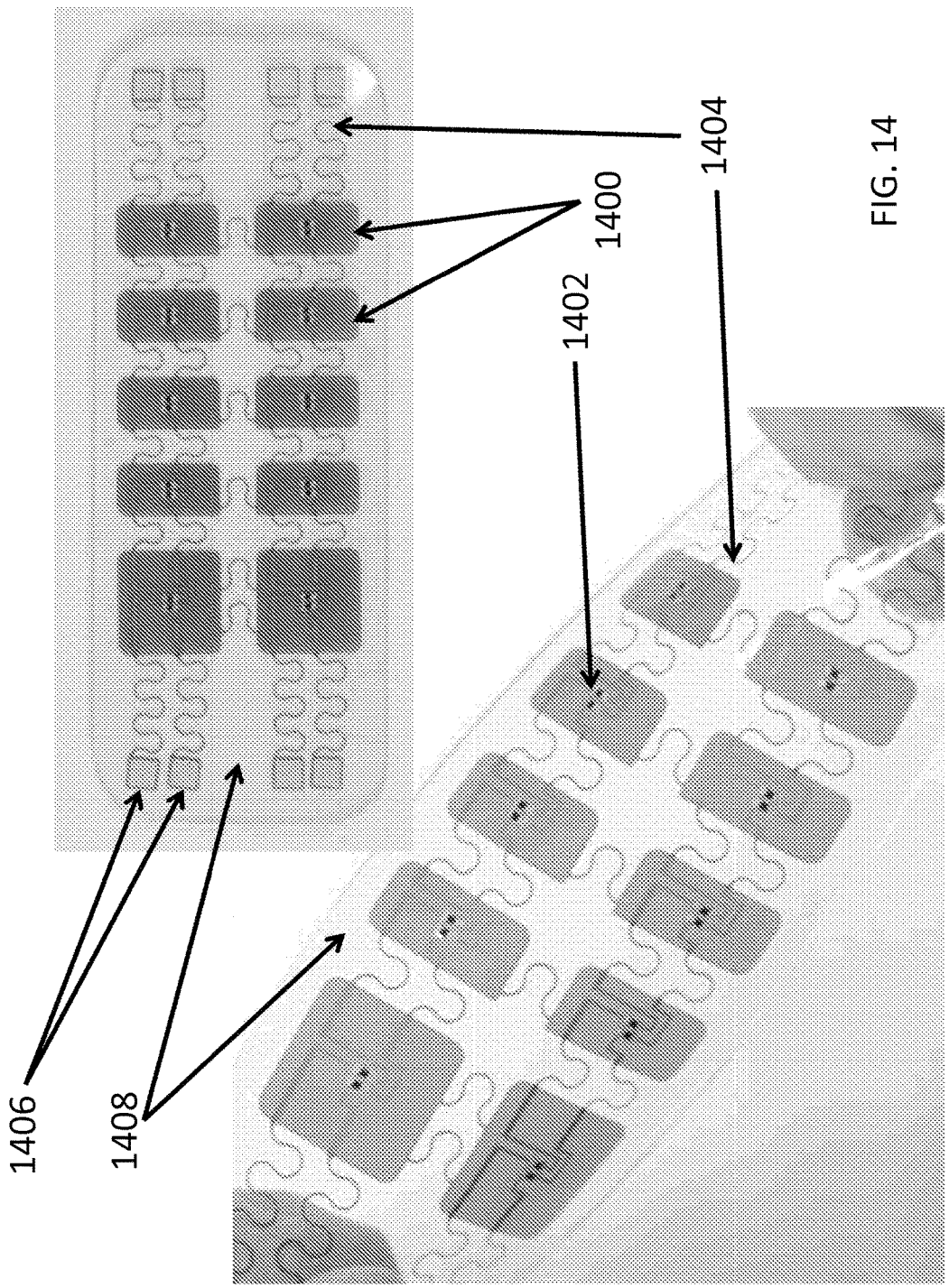
FIG. 14 shows an example stretchable device according to the principles described herein.

FIG. 14 shows a non-limiting example implementation of a stretchable device that includes device islands 1400, a discrete operative device component 1402 disposed on the device island 1400, and interconnects 1404 coupled to a portion of a device island 1400 and/or to an electrical contact 1406. The example stretchable device can include an encapsulant 1408 disposed over at least a portion of the discrete operative device 1402 and/or the interconnect 1404. In an example, the encapsulant can be but is not limited to a coating of an epoxy-based coverlay.

In any example implementation, the example stretchable device can be configured to control placement of a location of a spatially-varying neutral mechanical plane locally in the region of functional component of the stretchable device, including at least one of a device component, an interconnect, and a transition region between a device component and an interconnect. Controlled placement of the spatially-varying neutral mechanical plane relative to a functional component can result in little to no stress or strain being exerted in selected regions of the functional component, when the overall stretchable device is subjected to the deformation forces (including from an applied stress or strain). The positioning of the spatially-varying neutral mechanical plane can be controlled locally at any electronic component of the overall conformal device by controlling parameters locally including at least one of the following: to the shape of the interconnect, the placement of the encapsulant in the overall stretchable device, and the type of encapsulant material (degree of stiffness), the material composition and dimensions of the base plate, and the composition and modulus properties of the substrate.

Non-limiting example system architectures are described below relative to stretchable devices that are configured as conformal motion sensor systems. However, the example system architectures described herein are not so limited. The example system architectures below can be applicable to any type of conformal sensor system fabricated according to the principles described herein, including any one or more of a temperature sensor, a neuro-sensor, a hydration sensor, a heart sensor, a flow sensor, a pressure sensor, an equipment monitor (e.g., smart equipment), a respiratory rhythm monitor, a skin conductance monitor, an electrical contact, or any combination thereof, including a multifunctional sensor, such as but not limited to a temperature, strain, and/or electrophysiological sensor, a combined motion-/heart/neuro-sensor, a combined heart-/temperature-sensor, etc.

As a non-limiting example, the architecture of the conformal motion sensor system can include one or more sensors, power & power circuitry, wireless communication, and at least one processing unit. In some example, the power source can be a wireless power source.

FIGS. 15A-15D show non-limiting examples of possible device configurations. The example device of FIG. 15A includes a data receiver 1501 disposed on a substrate 1500. The data receiver 1501 can be configured to conform to a portion of the object to which the data receiver 1501 and the substrate are coupled. The object can be at least one body part, a secondary object, and/or a muscle group. The data receiver 1501 can include one or more of any conformal sensor component according to the principles of any of the examples and/or figures described herein. In an example, the data receiver includes at least one accelerometer 1503 and/or at least one muscle activation monitor 1504. The at least one accelerometer 1503 and/or at least one muscle activation monitor 1504 can be used to measure data indicative of a motion of an object (including a body part of a subject, a secondary object, and/or a muscle group). The example device of FIG. 15A also includes an analyzer 1502. The analyzer 1502 can be configured to quantify the data indicative of motion, physiological data, or analysis of such data indicative of motion, and physiological data, according to the principles described herein. In one example, the analyzer 1502 can be disposed on the substrate 1500 with the data receiver 1501, and in another example, the analyzer 1502 can be disposed proximate to the substrate 1500 and data receiver 1501.

In the example implementation of the device in FIG. 15A, the analyzer 1502 can be configured to quantify or otherwise analyze the data indicative of the accelerometry measurement and/or the muscle activation monitoring to provide an indication of a motion of the body part and/or muscle activity.

FIG. 15B shows another example device according to the principles disclosed herein that includes a substrate 1500, data receiver 1501, an analyzer 1502, and a storage module 1505. The storage module 1505 can be configured to include a memory to save data from the data receiver 1501 and/or the analyzer 1502. In some implementations the storage device 1505 is any type of non-volatile memory. For example, the storage device 1505 can include flash memory, solid state drives, removable memory cards, or any combination thereof. In certain examples, the storage device 1505 is removable from the device. In some implementations, the storage device 1505 is local to the device while in other examples it is remote. For example, the storage device 1505 can be the internal memory of a computing device. In the various examples herein, the computing device may be a smartphone, a tablet computer, a slate computer, an e-reader or other electronic reader or hand-held or wearable computing device, a laptop, an Xbox®, a Wii®, or other game system(s). In this example, the device may communicate with the external computing device via an application executing on the external computing device. In some implementations, the sensor data can be stored on the storage device 1505 for processing at a later time. In some examples, the storage device 1505 can include space to store processor-executable instructions that are executed to analyze the data from the data receiver 1501. In other examples, the memory of the storage device 1505 can be used to store the measured data indicative of motion, physiological data, or analysis of such data indicative of motion, or physiological data, according to the principles described herein.

Figure 15C:
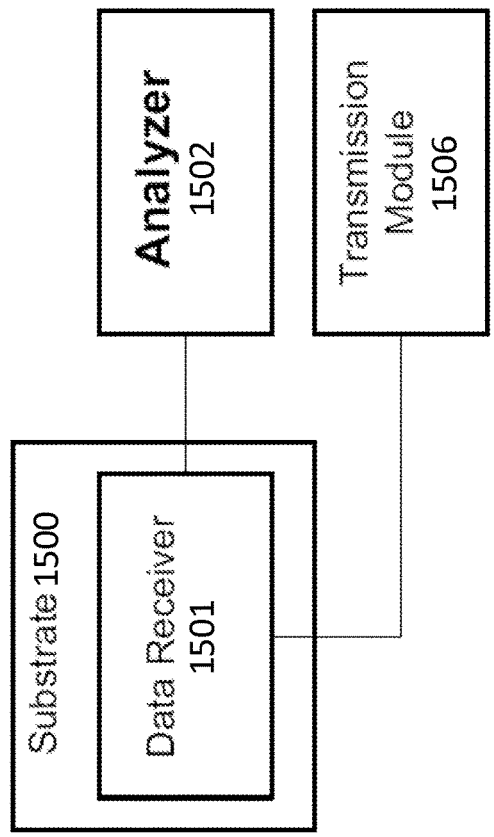

FIG. 15C shows an example device according to the principles disclosed herein that includes a substrate 1500, a data receiver 1501, an analyzer 1502, and a transmission module 1506. The transmission module 1506 can be configured to transmit data from the data receiver 1501, the analyzer 1502, or stored in a storage device (such as the storage device 1505 of FIG. 15B), to an external memory or other storage device, a network, and/or an off-board computing device. In one example, the transmission module 1506 can be a wireless transmission module. For example, the transmission module 1506 can be used to transmit data via wireless networks, radio frequency communication protocols, Bluetooth®, near-field communication (NFC), and/or optically using infrared or non-infrared LEDs. The data can be transmitted to an external memory or other storage device, a network, and/or an off-board computing device.

Figure 15D:
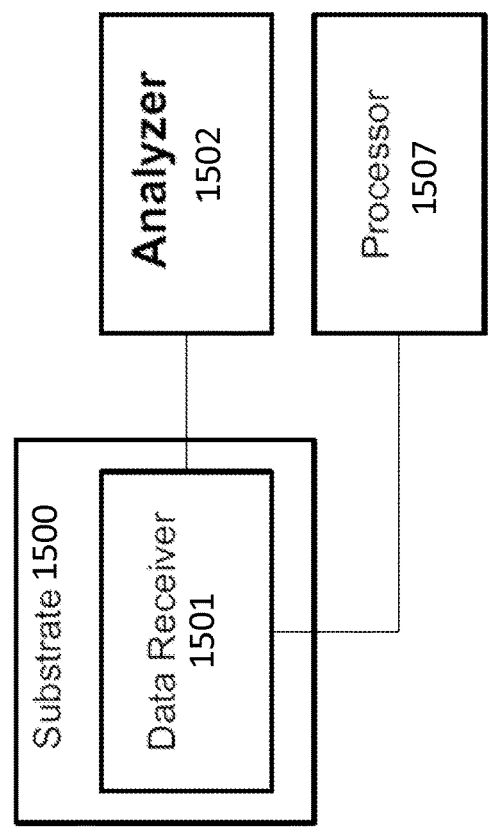

FIG. 15D shows an example system that includes a substrate 1500, a data receiver 1501, an analyzer 1502 and a processor 1507. The data receiver 1501 can receive data related to sensor measurement from a sensor. In an example, the sensor can be a conformal sensor. The processor 1507 can be configured to execute processor-executable instructions stored in a storage device 1507 and/or within the processor 1507 to analyze data indicative of motion, physiological data, or analysis of such data indicative of motion, or physiological data according to the principles described herein. In some implementations, the data can be directly received from the data receiver 1501 or retrieved from a storage device (such as the storage device 1505 of FIG. 15B). In one example, the processor can be a component of the analyzer 1502 and/or disposed proximate to the data receiver 1501. In another example, the processor 1507 can be external to the system, such as in a computing device that downloads and analyzes data retrieved from the system. The processor 1507 can execute processor-executable instructions that quantify the data received by the data receiver 1501.

Figure 16C:
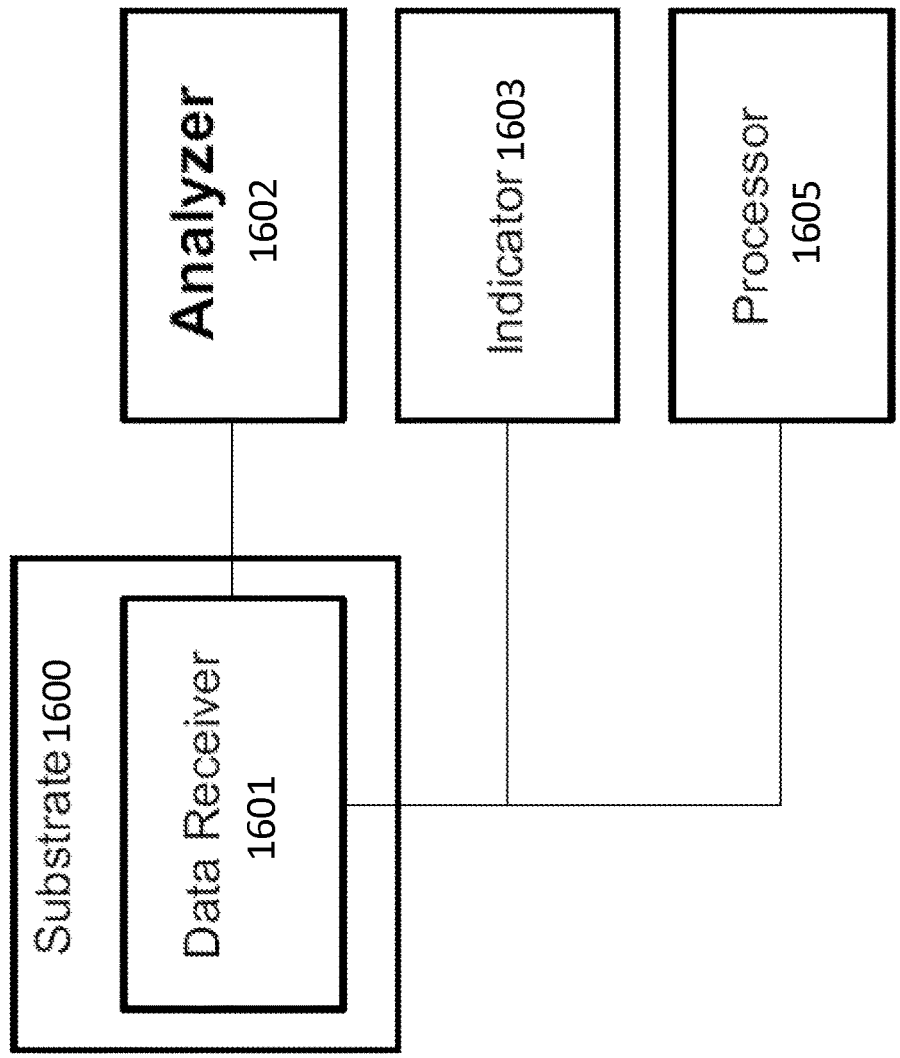

FIGS. 16A-16C show non-limiting examples of possible system configurations including a display for displaying or otherwise outputting the data or analysis results from analysis of the data. The example systems of FIGS. 16A-16C include a substrate 1600, a data receiver 1601, an analyzer 1602, and an indicator 1603. As shown in the examples of FIGS. 16B-16C, the system can further include a processor 1605 (see FIG. 16C), to execute the processor-executable instructions described herein, and/or a storage device 1604 (see FIG. 16B), for storing processor-executable instructions and/or data from the analyzer 1602 and/or one or more conformal sensors of the system.

The indicator 1603 of the example systems of FIGS. 16A-16C can be used for displaying and/or transmitting data indicative of motion, physiological data, or analysis of such data indicative of motion, or physiological data, according to the principles described herein, and/or user information. In one example, the indicator 1603 can comprise a liquid crystal display, or an electrophoeretic display (such as e-ink), and/or a plurality of indicator lights. For example, the indicator 1603 can include a series of LEDs. In some implementations, the LEDs range in color, such as from green to red. In this example, if performance does not meet a pre-determined threshold measure, a red indicator light can be activated and if the performance meets the pre-determined threshold measure, the green indicator light can be activated. In another example, indicator 1603 may include a screen or other display that can be used to display graphs, plots, icons, or other graphic or visual representations indicative of the data or analysis results from analysis of the data.

In some implementations, as described above, the signaling of the indicator 1603 is detectable to the human eye, and in other implementations, it is not detectable by the human eye but can be detected using an image sensor. The indicator 1603 may be configured to emit light outside the viable spectrum of the human eye (e.g., infrared) or too dim to be detected, as examples of indication methods substantially not detectable by the human eye. In these examples, the image sensor can be configured to detect such signals outside the viewing capabilities of a human eye. In various examples, the image sensor may be a component of a smartphone, a tablet computer, a slate computer, an e-reader or other electronic reader or hand-held or wearable computing device, a laptop, an Xbox®, a Wii®, or other game system(s).

Figure 17:
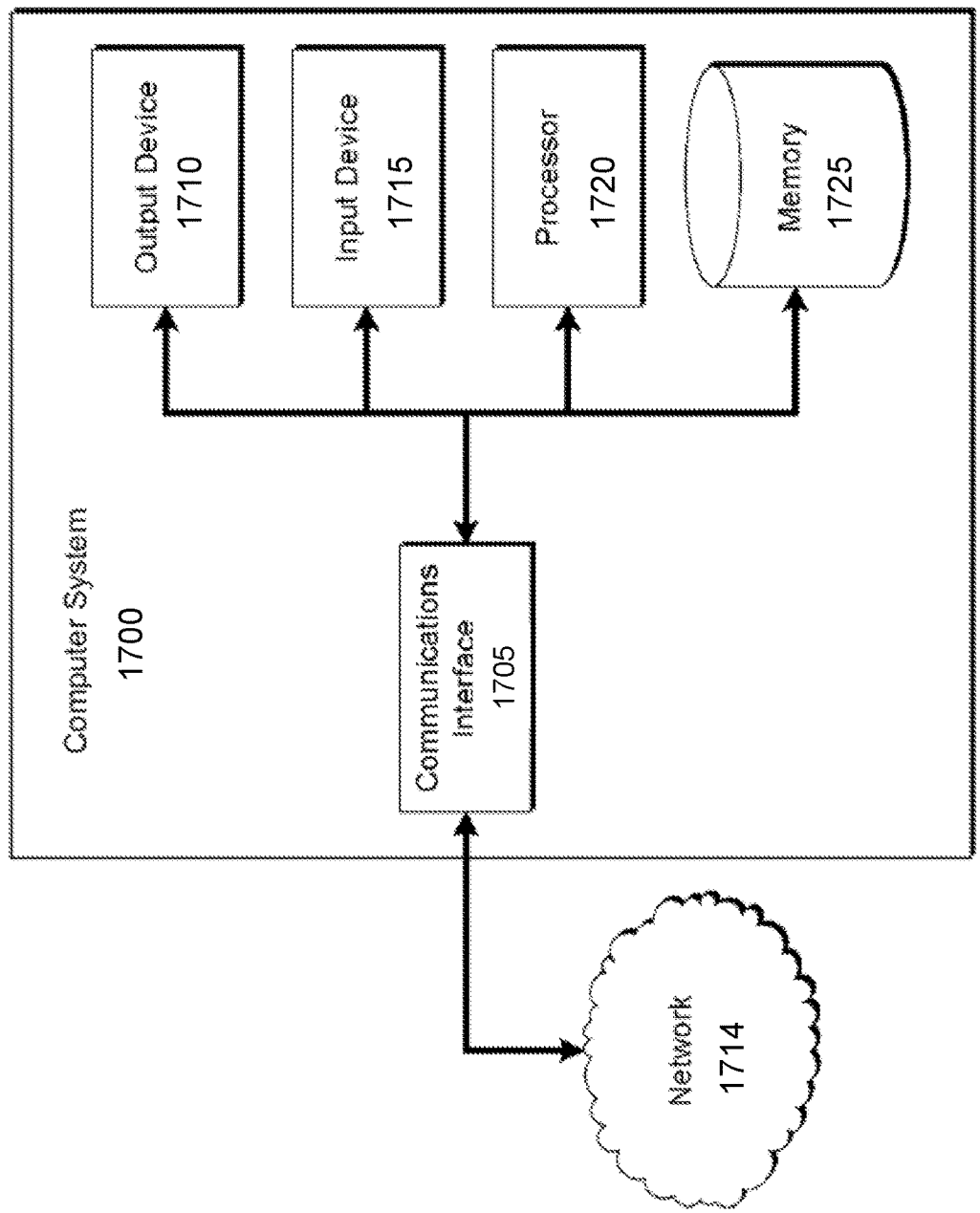
FIG. 17 shows the architecture of an example computer system according to the principles described herein.

FIG. 17 shows the architecture of an example computer system 1700 that may be employed to implement any of the example methods, computer systems, and apparatus discussed herein. The computer system 1700 of FIG. 17 includes one or more processors 1720 communicatively coupled to memory 1725, one or more communications interfaces 1705, and one or more output devices 1710 (e.g., one or more display units) and one or more input devices 1715.

In the computer system 1700 of FIG. 17, the memory 1725 may include any computer-readable storage media, and may store computer instructions such as processor-executable instructions for implementing the various functionalities described herein for respective systems, as well as any data relating thereto, generated thereby, or received via the communications interface(s) or input device(s). The processor(s) 1720 shown in FIG. 17 may be used to execute instructions stored in the memory 1725 and, in so doing, also may read from or write to the memory various information processed and or generated pursuant to execution of the instructions.

The processor 1720 of the computer system 1700 shown in FIG. 17 also may be communicatively coupled to or control the communications interface(s) 1705 to transmit and/or receive various information pursuant to execution of instructions. For example, the communications interface(s) 1705 may be coupled to a network 1714, and may therefore allow the computer system 1700 to transmit information to and/or receive information from other devices (e.g., other computer systems). Network 1714 can be a wired or wireless network, bus, or other data transmission means or communication means. The system of FIG. 17 may further include one or more communications interfaces to facilitate information flow between the components of the system 1700. In some implementations, the communications interface(s) may be configured (e.g., via various hardware components or software components) to provide a website as an access portal to at least some aspects of the computer system 1700.

The output devices 1710 of the computer system 1700 shown in FIG. 17 may be provided, for example, to allow various information to be viewed or otherwise perceived in connection with execution of the instructions. The input device(s) 1715 may be provided, for example, to allow a user to make manual adjustments, make selections, enter data or various other information, or interact in any of a variety of manners with the processor during execution of the instructions. The input device(s) 1715 may take the form of, but is not limited to, switches, contacts, capacitive or mechanical components. In other examples, input device(s) 1715 may use the measures from sensors to actuate controls of the system.

Figure 18:
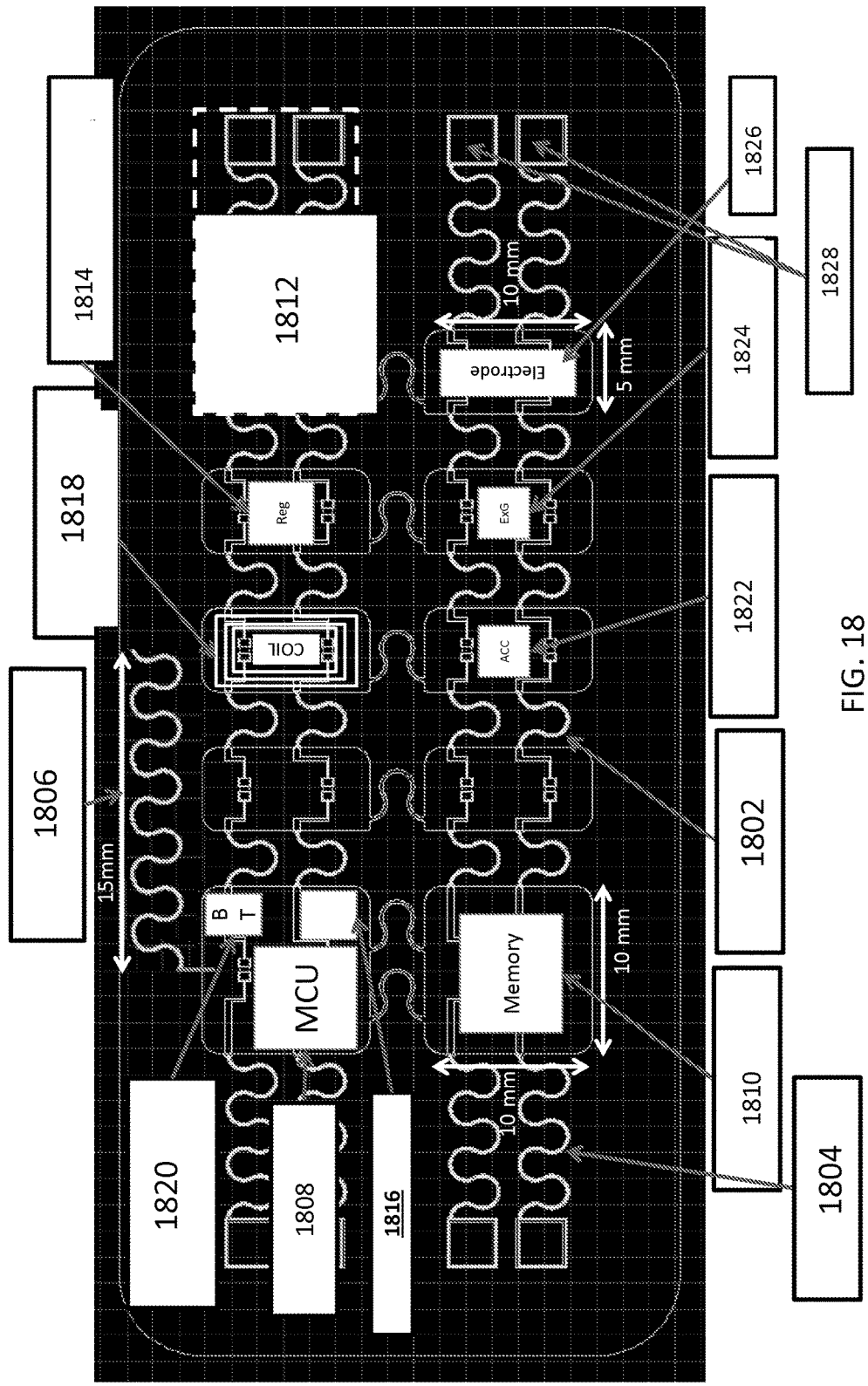
FIG. 18 shows an example conformal sensor device according to the principles described herein.

FIG. 18 shows an example schematic drawing of the mechanical layout and system-level architecture of a non-limiting example conformal motion sensor configured as a rechargeable patch. The example stretchable device includes a plurality of interconnects 1802 that couple to the device islands and interconnects 1804 that couple a device island to a contact. While FIG. 18 is interconnects 1802 and 1804 are shown as serpentine interconnects, any one or more of the fractal serpentine interconnects according to the principles described herein may be used as an interconnect 1802 or 1804. In an example, any interconnect 1802 or 1804 can be configured as a meander-shaped configuration including at least one nested serpentine-shaped feature. In an example, any interconnect 1802 or 1804 can be configured as a serpentine-shaped structure that includes at least one nested serpentine-shaped feature (a serpentine-in-serpentine configuration). The non-limiting example stretchable device also includes a monopole antenna 1806, which can be configured as any of the fractal serpentine interconnects according to the principles described herein. The example stretchable device can include multiple device components, such as a processor 1808, a memory 1810 in communication with the processor 1808, a power source 1812, regulators 1814 and 1816, a coil 1818, a communication component 1820, sensor components 1822 and 1824, an electrode 1826, and contacts 1828. In an example, the sensor component 1822 can be an accelerometer and the sensor component 1824 can be an EMG component. In an example, communication component 1820 can be a BLUETOOTH® device. In an example, coil 1818 can be a power transfer coil.

The example conformal motion sensor electronics technology can be designed and implemented with various mechanical and electrical layouts for multifunctional platforms. The devices including the conformal electronics technology integrate stretchable form factors using designs embedded in polymeric layers. These can be formulated to protect the circuits from strain and to achieve mechanical flexibility in an ultra-thin cross-section. For example, the device can be configured with thicknesses on the order of about 1 mm on average. In other examples, the patch can be configured with thinner or thicker cross-sectional dimensions. The device architecture can include a reusable module containing surface-mount technology (SMT) components, including accelerometer, wireless communication, microcontroller, antenna, coupled with disposable conformal electrode arrays for sensing EMG, EEG and EKG signals.

Conclusion

While various inventive embodiments have been described and illustrated herein, those of ordinary skill in the art will readily envision a variety of other means and/or structures for performing the function and/or obtaining the results and/or one or more of the advantages described herein, and each of such variations and/or modifications is deemed to be within the scope of the inventive embodiments described herein. More generally, those skilled in the art will readily appreciate that all parameters, dimensions, materials, and configurations described herein are meant to be examples and that the actual parameters, dimensions, materials, and/or configurations will depend upon the specific application or applications for which the inventive teachings is/are used. Those skilled in the art will recognize, or be able to ascertain using no more than routine experimentation, many equivalents to the specific inventive embodiments described herein. It is, therefore, to be understood that the foregoing embodiments are presented by way of example only and that inventive embodiments may be practiced otherwise than as specifically described. Inventive embodiments of the present disclosure are directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the inventive scope of the present disclosure.

The above-described embodiments of the invention may be implemented in any of numerous ways, including through implementations provided in Appendices A, B, C and D attached hereto. For example, some embodiments may be implemented using hardware, software or a combination thereof. When any aspect of an embodiment is implemented at least in part in software, the software code may be executed on any suitable processor or collection of processors, whether provided in a single device or computer or distributed among multiple devices/computers.

Also, the technology described herein may be embodied as a method, of which at least one example has been provided. The acts performed as part of the method may be ordered in any suitable way. Accordingly, embodiments may be constructed in which acts are performed in an order different than illustrated, which may include performing some acts simultaneously, even though shown as sequential acts in illustrative embodiments.

All definitions, as defined and used herein, should be understood to control over dictionary definitions, definitions in documents incorporated by reference, and/or ordinary meanings of the defined terms.

The indefinite articles "a" and "an," as used herein in the specification, unless clearly indicated to the contrary, should be understood to mean "at least one."

The phrase "and/or," as used herein in the specification, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of."

As used herein in the specification, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

What is claimed is:

1. A stretchable electrical device, comprising:
   two electrical contacts spaced apart by a distance; and
   an electrical interconnect connected to and extending from a first one of the two electrical contacts generally in a first direction and electrically coupling the first one of the two electrical contacts with a second one of the two electrical contacts;
   wherein the electrical interconnect has a meander-shaped base configuration comprising a plurality of repeated, connected, and alternating loops, each of the plurality of loops having a curved tip and a length extending from the curved tip in a second direction that is generally perpendicular to the first direction, each of the lengths connecting adjacent ones of the plurality of loops and each of the lengths forming a nested serpentine-shaped feature projecting in the first direction such that the electrical interconnect includes a plurality of nested serpentine-shaped features arranged along the electrical interconnect, each of the plurality of nested serpentine-shaped features being at least partially nested within an adjacent one of the plurality of nested serpentine-shaped features.

2. The stretchable electrical device of claim 1, wherein the two electrical contacts are disposed on an elastomeric substrate.

3. The stretchable electrical device of claim 2, wherein the two electrical contacts are in physical communication with the elastomeric substrate, and wherein the electrical interconnect is not in physical communication with the substrate.

4. The stretchable electrical device of claim 1, wherein at least one of the two electrical contacts is in communication with a semiconductor circuit.

5. The stretchable electrical device of claim 1, wherein the electrical contacts are metal contacts.

6. The stretchable electrical device of claim 1, further comprising at least one device component in communication with at least one of the two electrical contacts, and wherein the at least one device component is an electronic device component, an optical device component, an optoelectronic device component, a mechanical device component, a microelectromechanical device component, a nanoelectromechanical device component, a microfluidic device component or a thermal device.

7. The stretchable electrical device of claim 1, wherein the meander-shaped base configuration has a base amplitude and a base wavelength and wherein each of the plurality of nested serpentine-shaped features has (i) a nested amplitude that is less than the base amplitude, and (ii) a nested wavelength that is less than the base wavelength.

8. A stretchable device, comprising:
a stretchable substrate; and
a stretchable electronic circuit disposed on a surface of the stretchable substrate, the stretchable electronic circuit comprising:
a first discrete operative device;
a second discrete operative device spaced apart from the first discrete operating device by a distance; and
a stretchable electrical interconnect connected to and extending from the first discrete operating device generally in a first direction and electrically coupling the first discrete operative device to the second discrete operative device,
wherein the stretchable electrical interconnect has a meander-shaped base configuration comprising a plurality of repeated, connected, and alternating loops, each of the plurality of loops having a curved tip and a length extending from the curved tip in a second direction that is generally perpendicular to the first direction, each of the lengths connecting adjacent ones of the plurality of loops and each of the lengths forming a nested serpentine-shaped feature projecting in the first direction such that the electrical interconnect includes a plurality of nested serpentine-shaped features arranged along the electrical interconnect, each of the plurality of nested serpentine-shaped features being at least partially nested within an adjacent one of the plurality of nested serpentine-shaped features.

9. The stretchable device of claim 8, wherein the first discrete operative device or the second discrete operative device includes a metal contact.

10. The stretchable device of claim 8, wherein the first discrete operative device or the second discrete operative device is a semiconductor device.

11. The stretchable device of claim 8, wherein the first discrete operative device, the second discrete operative device, and the stretchable electrical interconnect are fabricated from a same material.

12. The stretchable device of claim 11, wherein the same material is a semiconductor material.

13. The stretchable device of claim 8, wherein the stretchable electrical interconnect is made from a semiconductor material.

14. The stretchable device of claim 8, wherein the first discrete operative device is formed from a first semiconductor material, and wherein the stretchable electrical interconnect is made from a second semiconductor material different from the first semiconductor material.

15. The stretchable device of claim 12, wherein the semiconductor material is a single crystal semiconductor material.

16. The stretchable device of claim 8, wherein the first discrete operative device and the second discrete operative device are in physical communication with the surface of the stretchable substrate, and wherein the stretchable electrical interconnect is not in physical communication with the surface.

17. The stretchable device of claim 8, wherein the first discrete operative device or the second discrete operative device comprises one or more of a photodetector, a photodiode array, a display, a light-emitting device, a photovoltaic device, a sensor array, a light-emitting diode, a semiconductor laser, an optical imaging system, a transistor, a microprocessor, an integrated circuit, or any combination of thereof.

18. A stretchable electrical device, comprising:
two electrical contacts spaced apart by a distance; and
an electrical interconnect connected to and extending from a first one of the two electrical contacts generally in a first direction and electrically coupling the first one of the two electrical contacts with a second one of the two electrical contacts;
wherein the electrical interconnect has a meander-shaped base configuration comprising a plurality of repeated, connected, and alternating loops, each of the plurality of loops having a curved tip and a length extending from the curved tip, wherein the plurality of loops includes (i) a first set of curved tips generally disposed on a first side of the electrical interconnect and (ii) a second set of curved tips generally disposed on a second opposing side of the electrical interconnect, each of the lengths forming a nested serpentine-shaped feature, each of the nested serpentine-shaped features being disposed between the first side of the electrical interconnect and the second side of the electrical interconnect such that the electrical interconnect includes a plurality of nested serpentine-shaped features arranged along the electrical interconnect, each of the plurality of nested serpentine-shaped features being at least partially nested within an adjacent one of the plurality of nested serpentine-shaped features.

* * * * *